United States Patent
Meller et al.

(10) Patent No.: US 9,903,820 B2
(45) Date of Patent: Feb. 27, 2018

(54) CHEMICAL FUNCTIONALIZATION OF SOLID-STATE NANOPORES AND NANOPORE ARRAYS AND APPLICATIONS THEREOF

(71) Applicant: The Trustees of Boston University, Boston, MA (US)

(72) Inventors: Amit Meller, Brookline, MA (US); Meni Wanunu, Cambridge, MA (US)

(73) Assignee: The Trustees of Boston University, Boston, MA (US)

( * ) Notice: Subject to any disclaimer, the term of this patent is extended or adjusted under 35 U.S.C. 154(b) by 51 days.

(21) Appl. No.: 14/815,727

(22) Filed: Jul. 31, 2015

(65) Prior Publication Data

US 2016/0103067 A1   Apr. 14, 2016

Related U.S. Application Data

(62) Division of application No. 12/599,440, filed as application No. PCT/US2008/063066 on May 8, 2008, now Pat. No. 9,121,843.

(Continued)

(51) Int. Cl.
  *G01N 25/18* (2006.01)
  *G01N 21/64* (2006.01)
  (Continued)

(52) U.S. Cl.
  CPC .......... *G01N 21/6428* (2013.01); *B82Y 15/00* (2013.01); *C12Q 1/6869* (2013.01);
  (Continued)

(58) Field of Classification Search
  None
  See application file for complete search history.

(56) References Cited

U.S. PATENT DOCUMENTS 4,161,690 A   7/1979   Feier
4,962,037 A   10/1990  Jett et al.
(Continued)

FOREIGN PATENT DOCUMENTS

CN   1403817 A    3/2003
CN   201302544 Y  9/2009
(Continued)

OTHER PUBLICATIONS

Akeson et al., "Microsecond Time-Scale Discrimination Among Polycytidylic Acid, Polyadenylic Acid, and Polyuridylic Acid as Homopolymers or as Segments Within Single RNA Molecules," Bophysical Journal. 77: Dec. 1999, pp. 3327-3233.

(Continued)

*Primary Examiner* — Xiaoyun R Xu
(74) *Attorney, Agent, or Firm* — Wilmer Cutler Pickering Hale and Dorr LLP

(57) ABSTRACT

Chemical functionalization of solid-state nanopores and nanopore arrays and applications thereof. Nanopores are extremely sensitive single-molecule sensors. Recently, electron beams have been used to fabricate synthetic nanopores in thin solid-state membranes with sub-nanometer resolution. A new class of chemically modified nanopore sensors are provided with two approaches for monolayer coating of nanopores by: (1) self-assembly from solution, in which nanopores ~10 nm diameter can be reproducibly ceased, and (2) self-assembly under voltage driven electrolyte flow, in which 5 nm nanopore may be coated. Applications of chemically modified nanopore are provided including, the detection of biopolymers such as DNA and RNA, immobilizing enzymes or other proteins for detection or for generating chemical gradients; and localized pH sensing.

9 Claims, 18 Drawing Sheets

Related U.S. Application Data

(60) Provisional application No. 60/928,160, filed on May 8, 2007, provisional application No. 60/928,260, filed on May 8, 2007, provisional application No. 60/928,158, filed on May 8, 2007.

(51) Int. Cl.
  *B82Y 15/00* (2011.01)
  *G01N 33/487* (2006.01)
  *C12Q 1/68* (2018.01)

(52) U.S. Cl.
  CPC .......... *G01N 33/48721* (2013.01); *G01N 2021/6439* (2013.01); *Y10T 428/2982* (2015.01); *Y10T 436/143333* (2015.01)

(56) References Cited

U.S. PATENT DOCUMENTS

| | | |
|---|---|---|
| 5,131,755 A | 7/1992 | Chadwick et al. |
| 5,202,290 A | 4/1993 | Moskovits |
| 5,356,776 A | 10/1994 | Kambara et al. |
| 5,387,926 A | 2/1995 | Bellan |
| 5,405,747 A | 4/1995 | Jett et al. |
| 5,470,705 A | 11/1995 | Grossman et al. |
| 5,580,732 A | 12/1996 | Grossman et al. |
| 5,624,800 A | 4/1997 | Grossman et al. |
| 5,795,782 A | 8/1998 | Church et al. |
| 5,798,042 A | 8/1998 | Chu et al. |
| 5,821,058 A | 10/1998 | Smith et al. |
| 5,945,312 A | 8/1999 | Goodman et al. |
| 5,989,871 A | 11/1999 | Grossman et al. |
| 6,015,714 A | 1/2000 | Baldarelli et al. |
| 6,136,543 A | 10/2000 | Anazawa et al. |
| 6,210,896 B1 | 4/2001 | Chan |
| 6,211,955 B1 | 4/2001 | Basiji et al. |
| 6,249,341 B1 | 6/2001 | Basiji et al. |
| 6,251,303 B1 | 6/2001 | Bawendi et al. |
| 6,252,303 B1 | 6/2001 | Huang |
| 6,263,286 B1 | 7/2001 | Gilmanshin et al. |
| 6,267,872 B1 | 7/2001 | Akeson et al. |
| 6,325,968 B1 | 12/2001 | Fricker et al. |
| 6,335,420 B1 | 1/2002 | Bruening et al. |
| 6,335,440 B1 | 1/2002 | Lee et al. |
| 6,355,420 B1 | 3/2002 | Chan |
| 6,362,002 B1 | 3/2002 | Denison et al. |
| 6,413,792 B1 | 7/2002 | Sauer et al. |
| 6,426,231 B1 | 7/2002 | Bayley et al. |
| 6,428,959 B1 | 8/2002 | Deamer |
| 6,429,897 B2 | 8/2002 | Derndinger et al. |
| 6,447,724 B1 | 9/2002 | Jensen et al. |
| 6,464,842 B1 | 10/2002 | Golovchenko et al. |
| 6,465,193 B2 | 10/2002 | Akeson et al. |
| 6,473,176 B2 | 10/2002 | Basiji et al. |
| 6,498,010 B1 | 12/2002 | Fitzgerald et al. |
| 6,503,757 B1 | 1/2003 | Chow |
| 6,504,943 B1 | 1/2003 | Sweatt et al. |
| 6,511,802 B1 | 1/2003 | Albrecht et al. |
| 6,528,258 B1 | 3/2003 | Russell |
| 6,537,755 B1 | 3/2003 | Drmanac |
| 6,583,865 B2 | 6/2003 | Basiji et al. |
| 6,608,680 B2 | 8/2003 | Basiji et al. |
| 6,608,682 B2 | 8/2003 | Ortyn et al. |
| 6,616,895 B2 | 9/2003 | Dugas et al. |
| 6,617,113 B2 | 9/2003 | Deamer |
| 6,618,140 B2 | 9/2003 | Frost et al. |
| 6,618,679 B2 | 9/2003 | Loehrlein et al. |
| 6,627,067 B1 | 9/2003 | Branton et al. |
| 6,671,044 B2 | 12/2003 | Ortyn et al. |
| 6,673,615 B2 | 1/2004 | Denison et al. |
| 6,706,203 B2 | 3/2004 | Barth et al. |
| 6,723,515 B2 | 4/2004 | Barron |
| 6,743,905 B2 | 6/2004 | Woo et al. |
| 6,746,594 B2 | 6/2004 | Akeson et al. |
| 6,752,914 B1 | 6/2004 | Hassard |
| 6,756,204 B2 | 6/2004 | Grossman et al. |
| 6,758,961 B1 | 7/2004 | Vogel et al. |
| 6,772,070 B2 | 8/2004 | Gilmanshin et al. |
| 6,790,671 B1 | 9/2004 | Austin et al. |
| 6,821,726 B1 | 11/2004 | Dahm et al. |
| 6,824,659 B2 | 11/2004 | Bayley et al. |
| 6,830,670 B1 | 12/2004 | Viovy et al. |
| 6,855,551 B2 | 2/2005 | Bawendi et al. |
| 6,856,390 B2 | 2/2005 | Nordman et al. |
| 6,906,749 B1 | 6/2005 | Fox |
| 6,916,665 B2 | 7/2005 | Bayley et al. |
| 6,936,433 B2 | 8/2005 | Akeson et al. |
| 6,947,128 B2 | 9/2005 | Basiji et al. |
| 6,952,651 B2 | 10/2005 | Su |
| 6,975,400 B2 | 12/2005 | Ortyn et al. |
| 6,982,146 B1 | 1/2006 | Schneider et al. |
| 6,998,251 B2 | 2/2006 | Guttman et al. |
| 7,001,792 B2 | 2/2006 | Sauer et al. |
| 7,005,264 B2 | 2/2006 | Su et al. |
| 7,008,547 B2 | 3/2006 | Chen et al. |
| 7,049,104 B2 | 5/2006 | Kambara et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,060,507 B2 | 6/2006 | Akeson et al. |
| 7,074,569 B2 | 7/2006 | Woo et al. |
| 7,129,050 B2 | 10/2006 | Grossman et al. |
| 7,189,503 B2 | 3/2007 | Akeson et al. |
| 7,201,836 B2 | 4/2007 | Vogel et al. |
| 7,235,184 B2 | 6/2007 | Dugas et al. |
| 7,235,361 B2 | 6/2007 | Bawendi et al. |
| 7,238,485 B2 | 7/2007 | Akeson et al. |
| 7,244,349 B2 | 7/2007 | Vogel et al. |
| 7,248,771 B2 | 7/2007 | Schmidt et al. |
| 7,250,115 B2 | 7/2007 | Barth |
| 7,271,896 B2 | 9/2007 | Chan et al. |
| 7,279,337 B2 | 10/2007 | Zhu |
| 7,280,207 B2 | 10/2007 | Oldham et al. |
| 7,285,010 B2 | 10/2007 | Hatakeyama et al. |
| 7,364,851 B2 | 4/2008 | Berlin et al. |
| 7,371,533 B2 | 5/2008 | Slater et al. |
| 7,381,315 B2 | 6/2008 | Grossman et al. |
| 7,387,715 B2 | 6/2008 | Vogel et al. |
| 7,390,457 B2 | 6/2008 | Schembri |
| 7,397,232 B2 | 7/2008 | Hu et al. |
| 7,410,564 B2 | 8/2008 | Flory |
| 7,428,047 B2 | 9/2008 | Oldham et al. |
| 7,438,193 B2 | 10/2008 | Yang et al. |
| 7,444,053 B2 | 10/2008 | Schmidt et al. |
| 7,468,271 B2 | 12/2008 | Golovchenko et al. |
| 7,476,503 B2 | 1/2009 | Turner et al. |
| 7,553,730 B2 | 6/2009 | Barth et al. |
| 7,567,695 B2 | 7/2009 | Frost et al. |
| 7,595,023 B2 | 9/2009 | Lewis et al. |
| 7,609,309 B2 | 10/2009 | Brown et al. |
| 7,622,934 B2 | 11/2009 | Hibbs et al. |
| 7,625,706 B2 | 12/2009 | Akeson et al. |
| 7,651,599 B2 | 1/2010 | Blaga et al. |
| 7,666,593 B2 | 2/2010 | Lapidus |
| 7,670,770 B2 | 3/2010 | Chou et al. |
| 7,678,562 B2 | 3/2010 | Ling |
| 7,744,816 B2 | 6/2010 | Su et al. |
| 7,777,505 B2 | 8/2010 | White et al. |
| 7,803,607 B2 | 9/2010 | Branton et al. |
| 7,835,870 B2 | 11/2010 | Nair et al. |
| 7,838,873 B2 | 11/2010 | Clevenger et al. |
| 7,843,562 B2 | 11/2010 | Chan et al. |
| 7,846,738 B2 | 12/2010 | Golovchenko et al. |
| 7,849,581 B2 | 12/2010 | White et al. |
| 7,871,777 B2 | 1/2011 | Schneider et al. |
| 7,883,869 B2 | 2/2011 | Ju et al. |
| 7,897,338 B2 | 3/2011 | Woo et al. |
| 7,947,454 B2 | 5/2011 | Akeson et al. |
| 7,972,858 B2 | 7/2011 | Meller et al. |
| 8,105,846 B2 | 1/2012 | Bayley et al. |
| 8,206,568 B2 | 6/2012 | Branton et al. |
| 8,394,584 B2 | 3/2013 | Timp et al. |
| 8,394,640 B2 | 3/2013 | Golovchenko et al. |
| 8,435,775 B2 | 5/2013 | Holliger et al. |

(56) References Cited

U.S. PATENT DOCUMENTS

| | | |
|---|---|---|
| 8,440,403 B2 | 5/2013 | Frayling |
| 8,771,491 B2 | 7/2014 | Huber |
| 8,802,838 B2 | 8/2014 | Meller et al. |
| 8,865,078 B2 | 10/2014 | Chiou et al. |
| 8,865,455 B2 | 10/2014 | Frayling |
| 9,121,843 B2 | 9/2015 | Meller et al. |
| 2002/0034762 A1 | 3/2002 | Muller et al. |
| 2002/0119455 A1 | 8/2002 | Chan |
| 2003/0003463 A1 | 1/2003 | Rothberg et al. |
| 2003/0064366 A1 | 4/2003 | Hardin et al. |
| 2003/0092005 A1 | 5/2003 | Levene et al. |
| 2003/0096220 A1 | 5/2003 | Lafferty et al. |
| 2003/0143614 A1 | 7/2003 | Drmanac |
| 2003/0148544 A1 | 8/2003 | Nie et al. |
| 2003/0174992 A1 | 9/2003 | Levene et al. |
| 2003/0207326 A1 | 11/2003 | Su et al. |
| 2003/0215881 A1 | 11/2003 | Bayley et al. |
| 2004/0002089 A1 | 1/2004 | Dubertret et al. |
| 2004/0033492 A1 | 2/2004 | Chen |
| 2004/0137158 A1 | 7/2004 | Kools et al. |
| 2004/0146430 A1 | 7/2004 | Dugas |
| 2004/0175710 A1 | 9/2004 | Haushalter |
| 2004/0214221 A1 | 10/2004 | Muehlegger et al. |
| 2005/0014154 A1 | 1/2005 | Weizenegger |
| 2005/0019784 A1 | 1/2005 | Su et al. |
| 2005/0095599 A1 | 5/2005 | Pittaro et al. |
| 2005/0130159 A1 | 6/2005 | Rigler et al. |
| 2005/0136408 A1 | 6/2005 | Tom-Moy et al. |
| 2005/0147992 A1 | 7/2005 | Quake et al. |
| 2005/0153284 A1 | 7/2005 | Foldes-Papp et al. |
| 2005/0164211 A1 | 7/2005 | Hannah |
| 2005/0186576 A1 | 8/2005 | Chan et al. |
| 2005/0186629 A1 | 8/2005 | Barth |
| 2005/0196876 A1 | 9/2005 | Chan et al. |
| 2005/0227239 A1 | 10/2005 | Joyce |
| 2005/0230356 A1 | 10/2005 | Empedocles et al. |
| 2005/0241933 A1 | 11/2005 | Branton et al. |
| 2005/0282229 A1 | 12/2005 | Su et al. |
| 2006/0003458 A1 | 1/2006 | Golovchenko et al. |
| 2006/0019247 A1 | 1/2006 | Su et al. |
| 2006/0019259 A1 | 1/2006 | Joyce |
| 2006/0057355 A1 | 3/2006 | Suzuki et al. |
| 2006/0063171 A1 | 3/2006 | Akeson et al. |
| 2006/0147942 A1 | 7/2006 | Buzby |
| 2006/0210995 A1 | 9/2006 | Joyce |
| 2006/0231419 A1 | 10/2006 | Barth et al. |
| 2006/0251371 A1 | 11/2006 | Schmidt et al. |
| 2006/0278580 A1 | 12/2006 | Striemer et al. |
| 2006/0292041 A1 | 12/2006 | Dugas et al. |
| 2007/0012865 A1 | 1/2007 | Katzir et al. |
| 2007/0037199 A1 | 2/2007 | Takahashi et al. |
| 2007/0042366 A1 | 2/2007 | Ling |
| 2007/0054276 A1 | 3/2007 | Sampson |
| 2007/0165217 A1 | 7/2007 | Johansson et al. |
| 2007/0172858 A1 | 7/2007 | Hardin et al. |
| 2007/0172865 A1 | 7/2007 | Hardin et al. |
| 2007/0190542 A1 | 8/2007 | Ling et al. |
| 2007/0190543 A1 | 8/2007 | Livak |
| 2007/0202008 A1 | 8/2007 | Schembri et al. |
| 2007/0215472 A1 | 9/2007 | Slater et al. |
| 2007/0218494 A1 | 9/2007 | Slater et al. |
| 2007/0224613 A1 | 9/2007 | Strathmann |
| 2007/0231795 A1 | 10/2007 | Su |
| 2007/0264623 A1 | 11/2007 | Wang et al. |
| 2007/0285843 A1 | 12/2007 | Tran |
| 2008/0025875 A1 | 1/2008 | Martin et al. |
| 2008/0032290 A1 | 2/2008 | Young |
| 2008/0050752 A1 | 2/2008 | Sun et al. |
| 2008/0121534 A1 | 5/2008 | White et al. |
| 2008/0187915 A1 | 8/2008 | Polonsky et al. |
| 2008/0193956 A1 | 8/2008 | Kricka et al. |
| 2008/0218184 A1 | 9/2008 | White et al. |
| 2008/0254995 A1 | 10/2008 | Kim et al. |
| 2008/0261204 A1 | 10/2008 | Lexow |
| 2008/0274905 A1 | 11/2008 | Greene |
| 2008/0311375 A1 | 12/2008 | Harnack et al. |
| 2009/0021735 A1 | 1/2009 | Oldham et al. |
| 2009/0024331 A1 | 1/2009 | Tomaney et al. |
| 2009/0029477 A1 | 1/2009 | Meller et al. |
| 2009/0035777 A1 | 2/2009 | Kokoris et al. |
| 2009/0061447 A1 | 3/2009 | Schneider |
| 2009/0066315 A1 | 3/2009 | Hu et al. |
| 2009/0136958 A1 | 5/2009 | Gershow et al. |
| 2009/0137007 A1 | 5/2009 | Korlach et al. |
| 2009/0148348 A1 | 6/2009 | Pettigrew et al. |
| 2009/0185955 A1 | 7/2009 | Nellissen |
| 2009/0222216 A1 | 9/2009 | Hibbs et al. |
| 2009/0250615 A1 | 10/2009 | Oldham et al. |
| 2009/0277869 A1 | 11/2009 | Dugas |
| 2009/0298075 A1 | 12/2009 | Travers et al. |
| 2009/0305278 A1 | 12/2009 | Hardin et al. |
| 2009/0314939 A1 | 12/2009 | Stern et al. |
| 2010/0025249 A1 | 2/2010 | Polonsky et al. |
| 2010/0029508 A1 | 2/2010 | Austin et al. |
| 2010/0035260 A1 | 2/2010 | Olasagasti et al. |
| 2010/0035268 A1 | 2/2010 | Beechem et al. |
| 2010/0075309 A1 | 3/2010 | Maxham et al. |
| 2010/0103416 A1 | 4/2010 | Oldham et al. |
| 2010/0227913 A1 | 9/2010 | Lyakhov et al. |
| 2010/0262379 A1 | 10/2010 | Frazier |
| 2010/0292101 A1 | 11/2010 | So |
| 2010/0331194 A1 | 12/2010 | Turner et al. |
| 2011/0053284 A1 | 3/2011 | Meller et al. |
| 2011/0172404 A1 | 7/2011 | Luo et al. |
| 2011/0177498 A1 | 7/2011 | Clarke et al. |
| 2011/0177978 A1 | 7/2011 | Luo et al. |
| 2011/0257043 A1 | 10/2011 | Meller et al. |
| 2011/0308950 A1 | 12/2011 | Sakai et al. |
| 2012/0055792 A1 | 3/2012 | Gundlach et al. |
| 2012/0135410 A1 | 5/2012 | Soni et al. |
| 2012/0199482 A1 | 8/2012 | Meller et al. |
| 2012/0261261 A1 | 10/2012 | Huber |
| 2013/0040827 A1 | 2/2013 | Macevicz |
| 2013/0176563 A1 | 7/2013 | Ozawa et al. |
| 2013/0203050 A1 | 8/2013 | Huber et al. |
| 2013/0203610 A1 | 8/2013 | Meller et al. |
| 2013/0256118 A1 | 10/2013 | Meller et al. |
| 2014/0087474 A1 | 3/2014 | Huber |
| 2014/0255935 A1 | 9/2014 | Huber |
| 2014/0367259 A1 | 12/2014 | Frayling et al. |
| 2015/0204840 A1 | 7/2015 | Soares et al. |

FOREIGN PATENT DOCUMENTS

| | | |
|---|---|---|
| WO | WO-2001/018247 | 3/2001 |
| WO | WO-2002068957 | 9/2002 |
| WO | WO-2004078640 A1 | 9/2004 |
| WO | WO-2005017025 A | 2/2005 |
| WO | WO-2005/045392 | 5/2005 |
| WO | WO-2005052591 A | 6/2005 |
| WO | WO-2005061373 A | 7/2005 |
| WO | WO-2006/020775 | 2/2006 |
| WO | WO-2006/052882 | 5/2006 |
| WO | WO-2006137891 A | 12/2006 |
| WO | WO-2008/049795 | 5/2008 |
| WO | WO-2008/092760 | 8/2008 |
| WO | WO-2009/007743 | 1/2009 |
| WO | WO-2009/020682 | 2/2009 |
| WO | WO-2009/056831 | 5/2009 |
| WO | WO-2009/092035 | 7/2009 |
| WO | WO-2010/002883 | 1/2010 |
| WO | WO-2010/007537 | 1/2010 |
| WO | WO-2010/116595 | 10/2010 |
| WO | WO-2011/040996 | 4/2011 |
| WO | WO-2011/050147 | 4/2011 |
| WO | WO-2011/067559 | 6/2011 |
| WO | WO-2011/126869 | 10/2011 |
| WO | WO-2012/121756 | 9/2012 |
| WO | WO-2012/170499 | 12/2012 |
| WO | WO-2014/066902 | 5/2014 |
| WO | WO-2014/066905 | 5/2014 |
| WO | WO-2014/190322 | 11/2014 |

(56) References Cited

FOREIGN PATENT DOCUMENTS

OTHER PUBLICATIONS

Bates et al., "Dynamics of DNA Molecules in a Membrane Channel Probed by Active Control Techniques," Biophysics J., 84: pp. 2366-2373, 2003.
Bezrukov et al., "Counting Polymers Moving Through a Single Ion Channel," Nature, 370, 1994, pp. 279-281.
Braha et al., "Simultaneous Stochastic Sensing of Divalent Metal Ions," Nat. Biotech, 17, 2000, pp. 1005-1007.
Fologea et al., "Detecting Single Stranded DNA with a Solid State Nanopore," Nano Letters, vol. 5, No. 10, 2005, pp. 1905-1909.
International Search Report and Written Opinion of the International Searching Authority, the European Patent Office, for PCT/US2008/063066, dated Mar. 15, 2010, 10 pages.
International Search Report and Written Opinion of the International Searching Authority, the United States Patent and Trademark Office, for PCT/US2010/034040, dated Jun. 24, 2010, 7 pages.
Kasianowicz et al., "Characterization of Individual Polynucleotide Molecules Using a Membrane Channel," Proc. Natl. Acad. Sc 93: 1996, pp. 13770-13773.
Kim et al., "Rapid Fabrication of Uniformly Sized Nanopores and Nanopore Arrays for Parallel DNA Analysis," Adv. Mater., 18, 2006, pp. 3149-3153.
Li et al., "Ion-Beam Sculpting at Nanometre Length Scales," Nature 412, 2001, pp. 166-169.
Meller et al., "Rapid Nanopore Discrimination between Single Polynucleotide Molecules," Proc. Nat. Acad. Sci. 97: pp. 1079-1084, 2000.
Meller et al., "Single Molecule Measurements of DNA Transport Through a Nanopore," Electrophoresis, 23: pp. 2583-2591, 2002.
Meller et al., "Voltage-Driven DNA Translocations through a Nanopore," Phys. Rev. Lett. 86: pp. 3435-3438, 2001.
Wanunu, et al., "Chemically Modified Solid-State Nanopores". Nano Letters, vol. 7, No. 6, pp. 1580-1585 (2007).
Zwolak et al., "Colloquium: Physical Approaches to DNA Sequencing and Detection," Rev. Mod Phys, vol. 80, 2008, pp. 141-165.
Aksimentiev et al., "Microscopic Kinetics of DNA Translocation through Synthetic Nanopores," Biophysical Journal vol. 87, pp. 2086-2097, Sep. 2004.
Algar and Krull, "Quantum dots as donors in fluorescence resonance energy transfer for the bioanalysis of nucleic acids, proteins, and other biological molecules," Anal. Bioanal. Chem., 391:1609-1618, 2008.
Anderson et al., "Incorporation of reporter-labeled nucleotides by DNA polymerases," Biotechniques, 38(2):257-263 (2005).
Augustin et al., "Progress towards single-molecule sequencing: enzymatic synthesis of nucleotide-specifically labeled DNA," J. Biotechnology, 86:289-301 (2001).
Baker et al., " Nanopores: A makeover for membranes," Nature Nanotechnology vol. 3, pp. 73-74, Feb. 2008.
Bayley, "Sequencing single molecules of DNA," Current Opinion in Chemical Biology,10(6):628-637, Dec. 2006.
Wu et al., "Microfluidic differential resistive pulse sensors," Electrophoresis, 29(13), pp. 2754-2759, 2008.
Yan et al., "Parallel Fabrication of Sub-50-nm Uniformly Sized Nanoparticles by Deposition through a Patterned Silicon Nitride Nanostencil," Nano Letters 5(6), pp. 1129-1134, 2005.
Yu et al., "Cyanine dye dUTP analogs for enzymatic labeling of DNA probes," Nucleic Acids Research 22(15):3226-3232 (1994).
Zhang et al., "Whole genome amplification from a single cell: implications for genetic analysis," Proc. Natl. Acad. Sci. USA vol. 89, No. 13, pp. 5847-5851, Jul. 1, 1992.
Brakmann and Löbermann, "High-density labeling of DNA: Preparation and characterization of the target material for single-molecule sequencing," Angew. Chem. Int. Ed., 40(8):1427-1429 (2001).
Brakmann, "High-Density Labeling of DNA for Single Molecule Sequencing," Methods in Molecular Biology 283:137-144 (2004).

Branton et al., "The potential and challenges of nanopore sequencing," Nature Biotechnology 26(10), pp. 1146-1153, Oct. 2008.
Butler et al., "Single-molecule DNA detection with an engineered MspA protein nanopore," Proceedings of the National Academy of Sciences 105(52), pp. 20647-20652, Dec. 30, 2008.
Chan et al., "DNA Mapping Using Microfluidic Stretching and Single-Molecule Detection of Fluorescent Site-Specific Tags," Genome Research vol. 14, pp. 1137-1146, 2004.
Chan et al., "Quantum Dot Bioconjugates for Ultrasensitive Nonisotopic Detection," Science vol. 281, pp. 2016-2018, Sep. 25, 1998.
Chansin et al., "Single-Molecule Spectroscopy Using Nanoporous Membranes," Nano Letters, vol. 7, No. 9; pp. 2901-2906, 2007.
Chen et al., "Atomic Layer Deposition to Fine-Tune the Surface Properties and Diameters of Fabricated Nanopores," Nano Letters 4(7), pp. 1333-1337, 2004.
Danelon et al., "Fabrication and Functionalization of Nanochannels by Electron-Beam-Induced Silicon Oxide Deposition," Langmuir vol. 22, pp. 10711-10715, 2006.
Deamer and Branton, "Characterization of Nucleic Acids by Nanopore Analysis," Acc. Chem. Res. 35(10), pp. 817-825, 2002.
Deamer and Akeson, "Nanopores and nucleic acids: prospects for ultrarapid sequencing," Trends in Biotechnology 18(4):147-151, Apr. 1, 2000.
Deblois and Bean, "Counting and Sizing of Submicron Particles by the Resistive Pulse Technique," Rev. Sci. Instruments 41(7), pp. 909-916, Jul. 1970.
Dekker, "Solid-state nanopores," Nature Nanotechnology vol. 2, pp. 209-215, Apr. 2007.
Dennis and Bao, "Quantum Dot—Fluorescent Protein Pairs as Novel Fluorescence Resonance Energy Transfer Probes," Nano Lett., vol. 8, No. 5, pp. 1439-1445, 2008.
Dörre et al., "Highly efficient single molecule detection in microstructures," J. Biotechnology 86:225-236 (2001).
Eigen et al., "Sorting single molecules: Application to diagnostics and evolutionary biotechnology," Proc. Natl. Acad. Sci., 91:5740-5747 (1994).
Etoh et al., "An Image Sensor Which Captures 100 Consecutive Frames at 1 000 000 Frames/s," IEEE Transactions on Electron Devices vol. 50. No. 1, pp. 144-151, Jan. 2003.
Földes-Papp et al., "Fluorescent high-density labeling of DNA: error-free substitution for a normal nucleotide," J. Biotechnology, 86:237-253 (2001).
Soni and Meller, "Progress toward Ultrafast DNA Sequencing Using Solid-State Nanopores," Clinical Chemistry vol. 53, No. 11, pp. 1996-2001, 2007.
Stephan et al., "Towards a general procedure for sequencing single DNA molecules," J. Biotechnology 86:255-267 (2001).
Gierlich et al., "Synthesis of Highly Modified DNA by a Combination of PCR with Alkyne-Bearing Triphosphates and Click Chemistry," Chem. Eur. J. vol. 13, pp. 9486-9494, 2007.
Giller et al., "Incorporation of reporter molecule-labeled nucleotides by DNA polymerases. I. Chemical synthesis of various reporter group-labeled 2'-deoxyribonucleoside-5'-triphosphates," Nucleic Acids Research 31(10):2630-2635 (2003).
Grayson et al., "A BioMEMS Review: MEMS Technology for Physiologically Integrated Devices," Proceedings IEEE 92(1), pp. 6-21, Jan. 2004.
Gupta P.K., "Single-molecule DNA sequencing technologies for future genomics research," Trends in Biotechnology 26(11), pp. 602-611, Nov. 1, 2008.
Ha et al., "Probing the interaction between two single molecules: fluorescence resonance energy transfer between a single donor and a single acceptor," Proc. Natl. Acad. Sci. USA, vol. 93, pp. 6264-6268, Jun. 1996.
He et al., "Single Nonblinking CdTe Quantum Dots Synthesized in Aqueous Thiopropionic Acid," Angew. Chem. Int. Ed. vol. 45, pp. 7588-7591, 2006.
Heins et al., "Detecting Single Porphyrin Molecules in a Conically Shaped Synthetic Nanopore," Nano Letters 5(9), pp. 1824-1829, 2005.

(56) References Cited

OTHER PUBLICATIONS

Heintzmann and Ficz, "Breaking the resolution limit in light microscopy," Briefings in Functional Genomics and Proteomics, 5(4):289-301 (2006).
Henriquez et al., "The resurgence of Coulter counting for analyzing nanoscale objects," The Analyst 129, pp. 478-482, 2004.
Song et al., "Structure of Staphylococcal α-Hemolysin, a Heptameric Transmembrane Pore," Science vol. 274, pp. 1859-1866, Dec. 13, 1996.
Holt and Jones, "The new paradigm of flow cell sequencing," Genome Research, vol. 18, pp. 839-846, 2008.
Iqbal et al., "Solid-state nanopore channels with DNA selectivity," Nature Nanotechnology pp. 1-6, Apr. 1, 2007.
Ito et al., "Observation of DNA transport through a single carbon nanotube channel using fluorescence microscopy," Chem. Comm. pp. 1482-1483, 2003.
Jagtiani et al., "A label-free high throughput resistive-pulse sensor for simultaneous differentiation and measurement of multiple particle-laden analytes," J. Micromech. Microeng. 16, pp. 1530-1539, 2006.
Johansson and Cook, "Intramolecular Dimers: A New Design Strategy for Fluorescence-Quenched Probes," Chem. Eur. J., 9:3466-3471 (2003).
Johansson, "Choosing Reporter-Quencher Pairs for Efficient Quenching Through Formation of Intramolecular Dimers," Methods in Molecular Biology 335:17-29 (2006).
Kang et al., "A storable encapsulated bilayer chip containing a single protein nanopore," J. Am. Chem. Soc. vol. 129, No. 15, pp. 4701-4705, Mar. 22, 2007.
Storm et al., "Fabrication of solid-state nanopores with single-nanometre precision," Nature Materials vol. 2, pp. 537-540, 2003.
Stryer, "Fluorescence Energy Transfer as a Spectroscopic Ruler," Annual Review of Biochemistry, vol. 47, pp. 819-846, 1978.
Tasara et al., "Incorporation of reporter molecule-labeled nucleotides by DNA polymerases. II. High density labeling of natural DNA," Nucleic Acids Research 31(10):2636-2646 (2003).
Kasianowicz et al., "Characterization of individual polynucleotide molecules using a membrane channel," Proc. Natl. Acad. Sci. USA vol. 93, pp. 13770-13773, Nov. 1996.
Kolb et al., "Click Chemistry: Diverse Chemical Function from a Few Good Reactions," Angew. Chem. Int. Ed., vol. 40, pp. 2004-2021, 2001.
Kristensen et al., "High-Throughput Methods for Detection of Genetic Variation," BioTechniques 30(2), pp. 318-332, Feb. 2001.
Lee et al., "High aspect ratio polymer microstructures and cantilevers for bioMEMS using low energy ion beam and photolithography," Sensors and Actuators A 71:144-149, Apr. 1998.
Levene et al., "Zero-mode waveguides for single-molecule analysis at high concentrations," Science, 299:682-686 (2003).
Li et al., "DNA Molecules and Configurations in a Solid-State Nanopore Microscope," Nat. Mater. vol. 2, pp. 611-615, 2003.
Zhu et al., "Directly labeled DNA probes using fluorescent nucleotides with different length linkers," Nucleic Acids Research 22(16):3418-3422 (1994).
Lin et al., "Recent Patents and Advances in the Next-Generation Sequencing Technologies," Recent Patents on Biomedical Engineering, vol. 1, No. 1, pp. 60-67, 2008.
Zhe et al., "A micromachined high throughput Coulter counter for bioparticle detection and counting," J. Micromech. Microeng. vol. 17, pp. 304-313, 2007.
Zheng et al., "Parallel analysis of biomolecules on a microfabricated capillary array chip," Electrophoresis vol. 27, abstract only (1 page), Mar. 2006.
Lo et al., "Fabrication of symmetric sub-5 nm nanopores using focused ion and electron beams," Nanotechnology vol. 17, No. 13, pp. 3264-3267, Jun. 2006.
Marras, "Interactive fluorophore and quencher pairs for labeling fluorescent nucleic acid hybridization probes," Molecular Biotechnology 38:247-255 (2008).
Marras, "Selection of fluorophore and quencher pairs for fluorescent nucleic acid hybridization probes," Methods in Molecular Biology 335:3-16 (2006).
Meagher et al., "Free-solution electrophoresis of DNA modified with drag-tags at both ends," Electrophoresis vol. 27, pp. 1702-1712, 2006.
Meagher et al., "Sequencing of DNA by Free-Solution Capillary Electrophoresis Using a Genetically Engineered Protein Polymer Drag-Tag," Anal. Chem. vol. 80, pp. 2842-2848, Apr. 15, 2008.
Medintz et al., "Quantum dot bioconjugates for imaging, labelling and sensing," Nature Materials 4:435-446 (2005).
Medintz et al., "A fluorescence resonance energy transfer-derived structure of a quantum dot-protein bioconjugate nanoassembly," PNAS 101(26), pp. 9612-9617, Jun. 29, 2004.
Vercoutere et al., "Rapid discrimination among individual DNA hairpin molecules at single-nucleotide resolution using an ion channel," Nature Biotechnology vol. 19, pp. 248-252, Mar. 2001.
Walker et al., "Key Residues for Membrane Binding, Oligomerization, and Pore Forming Activity of Staphylococcal α-Hemolysin Identified by Cysteine Scanning Mutagenesis and Targeted Chemical Modification," Journal of Biological Chemistry 270(39), pp. 23065-23071, Sep. 29, 1995.
Wang et al., "Nanopores with a spark for single-molecule detection," Nature Biotechnology vol. 19, pp. 622-623, Jul. 2001.
Mir, "Ultrasensitive RNA profiling: Counting single molecules on microarrays," Genome Research 16:1195-1197, 2006.
Mitchell and Howorka, "Chemical tags facilitate the sensing of individual DNA strands with nanopores," Angew. Chem. Int. Ed., 47:5565-5568, (2008).
Moerner and Fromm, "Methods of single-molecule fluorescence spectroscopy and microscopy," Review of Scientific Instruments 74(8):3597-3619 (2003).
Nakane et al., "Evaluation of nanopores as candidates for electronic analyte detection," Electrophoresis vol. 23, pp. 2592-2601, 2002.
Nakane et al., "Nanopore sensors for nucleic acid analysis," Journal of Physics: Condensed Matter 15(32), pp. R1365-R1393, 2003.
Ramachandran et al., "Current bursts in lipid bilayers initiated by colloidal quantum dots," Applied Physics Letters, 86:083901-1 to 083901-3, 2005.
Randolph and Waggoner, "Stability, specificity and fluorescence brightness of multiply-labeled fluorescent DNA probes," Nucleic Acids Research, 25(14):2923-2929 (1997).
Wanunu and Meller, "Chemically Modified Solid-State Nanopores," Nano Letters 7(6), pp. 1580-1585, 2007.
White et al., "Single Ion-Channel Recordings Using Glass Nanopore Membranes," J. Amer. Chem. Soc. 129:11766-11775, 2007.
Won et al., "Protein polymer drag-tags for DNA separations by end-labeled free solution electrophoresis," Electrophoresis vol. 26, pp. 2138-2148, 2005.
Rasnik et al., "Nonblinking and long-lasting single-molecule fluorescence imaging," Nature Methods 3(11), pp. 891-893, Nov. 2006.
Reed, "Quantum Dots," Scientific American, pp. 118-123, Jan. 1993.
Resch-Genger et al., "Quantum dots versus organic dyes as fluorescent labels," Nature Methods 5(9), pp. 763-775, Sep. 2008.
Rhee and Burns, "Nanopore Sequencing Technology: Nanopore Preparations," Trends in Biotechnology vol. 25, No. 4, pp. 174-181, Apr. 2007.
Rhee and Burns, "Nanopore sequencing technology: research trends and applications," Trends in Biotechnology vol. 24, No. 12, pp. 580-586, 2006.
Roy et al., "A practical guide to single molecule FRET," Nature Methods 5(6):507-516 (Jun. 2008).
Sabanayagam et al., "Long time scale blinking kinetics of cyanine fluorophores conjugated to DNA and its effect on Förster resonance energy transfer," J. Chem. Phys. 123(22), pp. 224708-1 to 224708-7, 2005.
Sanger et al., "DNA Sequencing with Chain-Terminating Inhibitors," Proc. Natl. Acad. Sci. USA, vol. 74, No. 12, pp. 5463-5467, Dec. 1977.

(56) References Cited

OTHER PUBLICATIONS

Sauer et al., "Single molecule DNA sequencing in submicrometer channels: state of the art and future prospects," J. Biotechnology 86:181-201 (2001).
Seela et al., "Fluorescent DNA: the development of 7-deazapurine nucleoside triphosphates applicable for sequencing at the single molecule level," J. Biotechnology, 86:269-279 (2001).
Shaffer, "Next-generation sequencing outpaces expectations," Nature Biotechnology vol. 25, p. 149, Feb. 2007.
Shi et al., "Luminescent Quantum Dots Fluorescence Resonance Energy Transfer-Based Probes for Enzymatic Activity and Enzyme Inhibitors," Anal. Chem. 79(1), pp. 208-214, Jan. 1, 2007.
Smolina et al., "High-density fluorescently labeled rolling-circle amplicons for DNA diagnostics," Analytical Biochemistry 347:152-155 (2005).
Visible Spectrum, Wikipedia, https://en.wikipedia.org/wiki/Visible_spectrum, accessed Mar. 3, 2017 (5 pages).
Pielou, E.C., "Chapter 10: Studying Pattern by Distance Sampling", in An Introduction to Mathematical Ecology, Wiley-Interscience A Division of John Wiley & Sons, New York, pp. 111-112, 1969 (4 pages).
Rottenfusser, R., et al., "Education in Microscopy and Digital Imaging: Numerical Aperture and Resolution", http://zeiss-campus.magnet.fsu.edu/articles/basics/resolution.html, accessed Mar. 3, 2017 (6 pages).
Bonnet et al., "Kinetics of conformational fluctuations in DNA hairpin-loops," P. Natl. Acad. Sci. USA, vol. 95, pp. 8602-8606 (1998).
Clarke et al., "Continuous Base Identification for Single-molecule Nanopore DNA Sequencing," Nature Nanotech, vol. 4, pp. 265-270 (2009).
Eid et al., "Real-Time DNA Sequencing from Single Polymerase Molecules," Science, vol. 323, pp. 133-138(2009).
Fuller et al., "The challenges of sequencing by synthesis," Nat. Biotech., vol. 27, pp. 1013-1023 (2009).
Green and Joynson, "A Preliminary Crystallographic Investigation of Avidin," Biochem. J., vol. 118, pp. 71-72 (1970), 3 pages.
Harris et al., "Single-Molecule DNA Sequencing of a Viral Genome," Science, vol. 320, pp. 106-109 (2008).
Healy, "Nanopore-based Single-molecule DNA Analysis," Nanomedicine, vol. 2, pp. 459-481 (2007).
Hopman et al., "Focused ion beam scan routine, dwell time and dose optimizations for submicrometre period planar photonic crystal components and stamps in silicon," Nanotechnology, vol. 18, No. 195305, 11 pgs. (2007).
Lee et al., "Electron Beam Projection Nanopatterning Using Crystal Lattice Images Obtained from High Resolution Transmission Electron Microscopy," Adv. Mater., vol. 19, pp. 4189-4193 (2007).
McNally et al., "Electromechanical Unzipping of Individual DNA Molecules Using Synthetic Sub-2 nm Pores," Nano Lett., vol. 8, pp. 3418-3422 (2008).
Nam et al., "Ionic Field Effect Transistors with Sub-10 nm Multiple Nanopores," Nano Lett., vol. 9, No. 5, pp. 2044-2048 (2009).
Shendure et al., "Advanced Sequencing Technologies: Methods and Goals," Nat. Rev. Genet., vol. 5, pp. 335-344 (2004), 18 pgs.
Soni et al., "Synchronous Optical and Electrical Detection of Biomolecules Traversing Through Solid-state Nanopores," Rev. Sci. Instrum., vol. 81, 9 pgs. (2010).
Tong et al., "Silicon Nitride Nanosieve Membrane," Nano Lett., vol. 4, No. 2, pp. 283-287 (2004).
Wanunu et al., "DNA Translocation Governed by Interactions with Solid-State Nanopores," Biophys. J., vol. 95, pp. 4716-4725 (2008).
Wanunu et al., "Electrostatic Focusing of Unlabelled DNA into Nanoscale Pores using a Salt Gradient," Advance Online Publication, Published in final edited form as: Nature Nanotech, vol. 5, No. 2, pp. 160-165 (2010).
Schlapak et al., "Glass Surfaces Grafted with High-Density Poly-(ethylene glycol) as Substrates for DNA Oligonucleotide Microarrays," Langmuir, 22, pp. 277-285 (2006).
Trepagnier et al., "Controlling DNA Capture and Propagation through Artificial Nanopores," Nano Letters, 7(9), pp. 2824-2830 (2007).

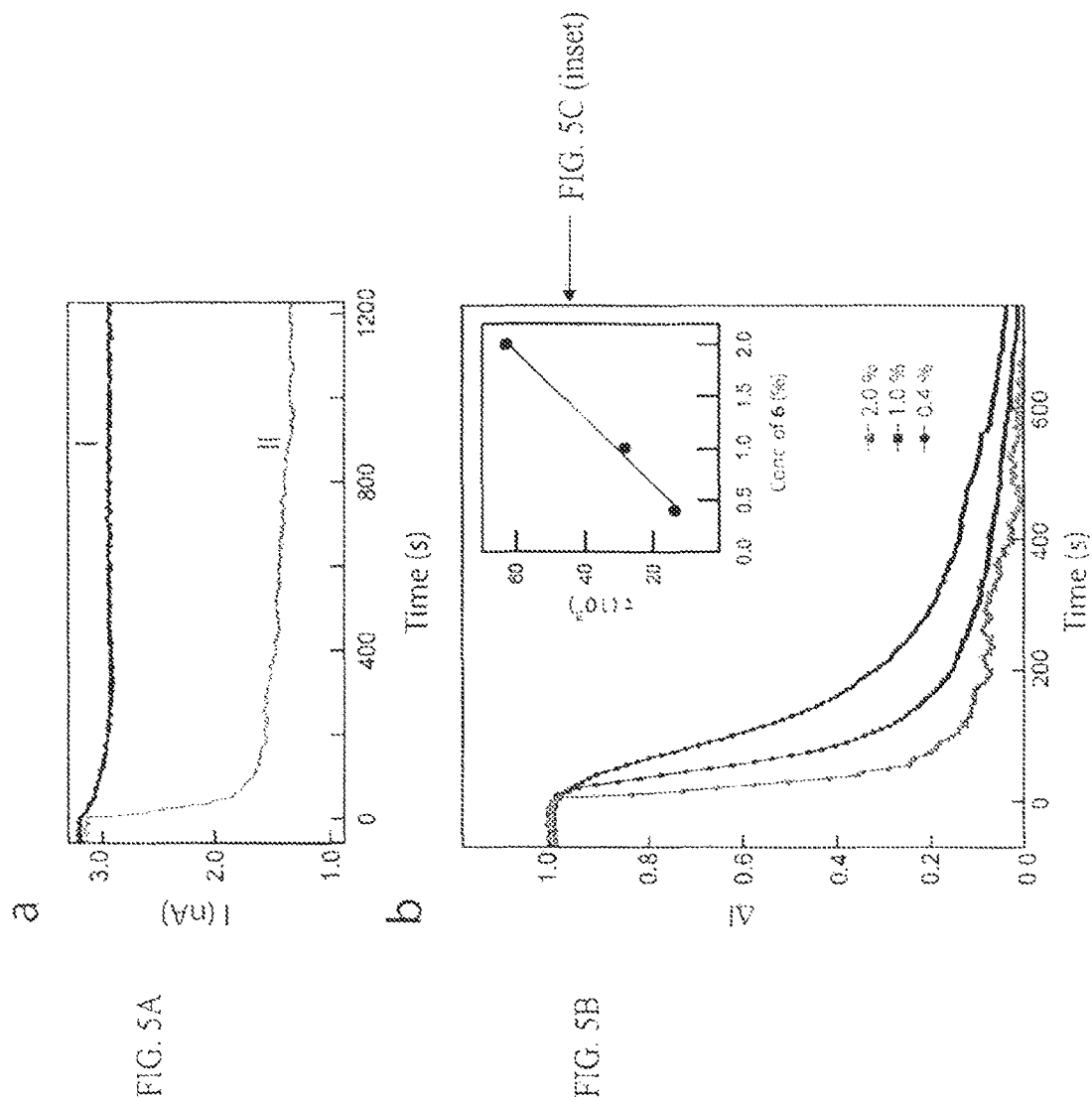

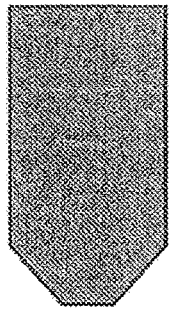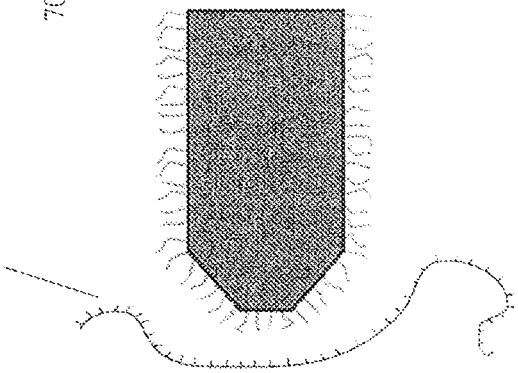
FIG. 7A
FIG. 7B

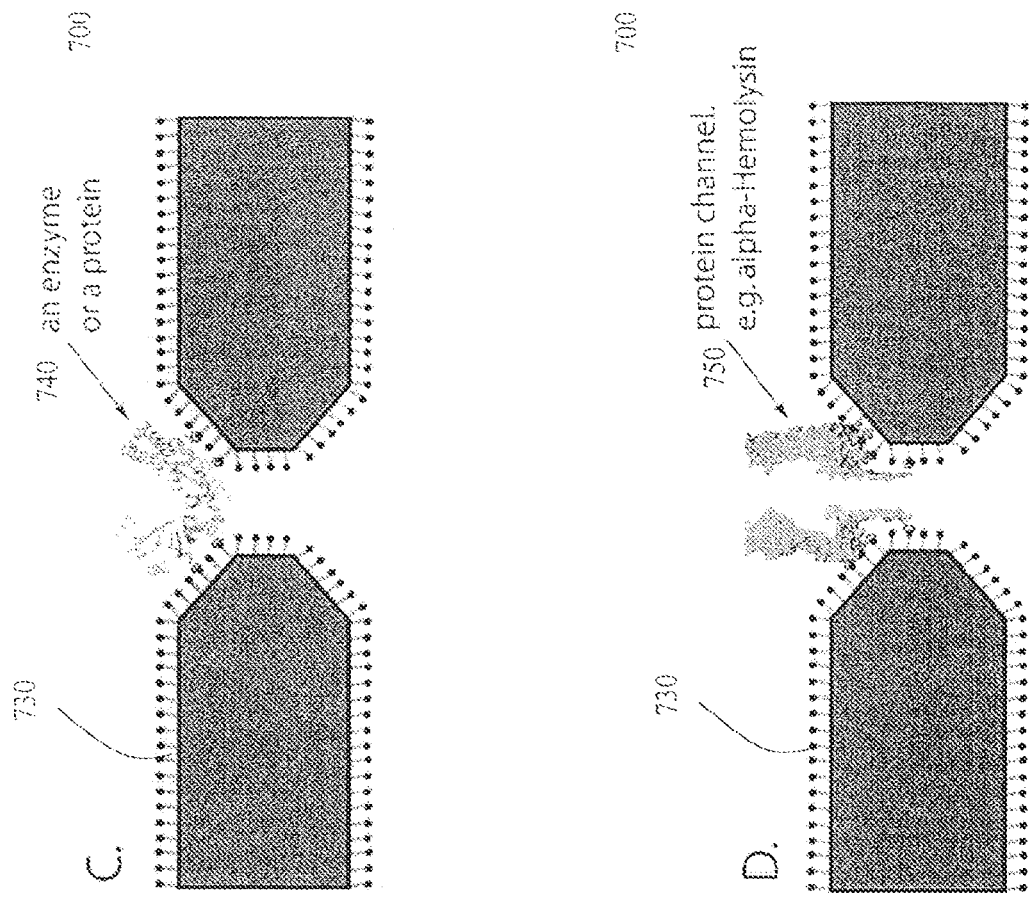

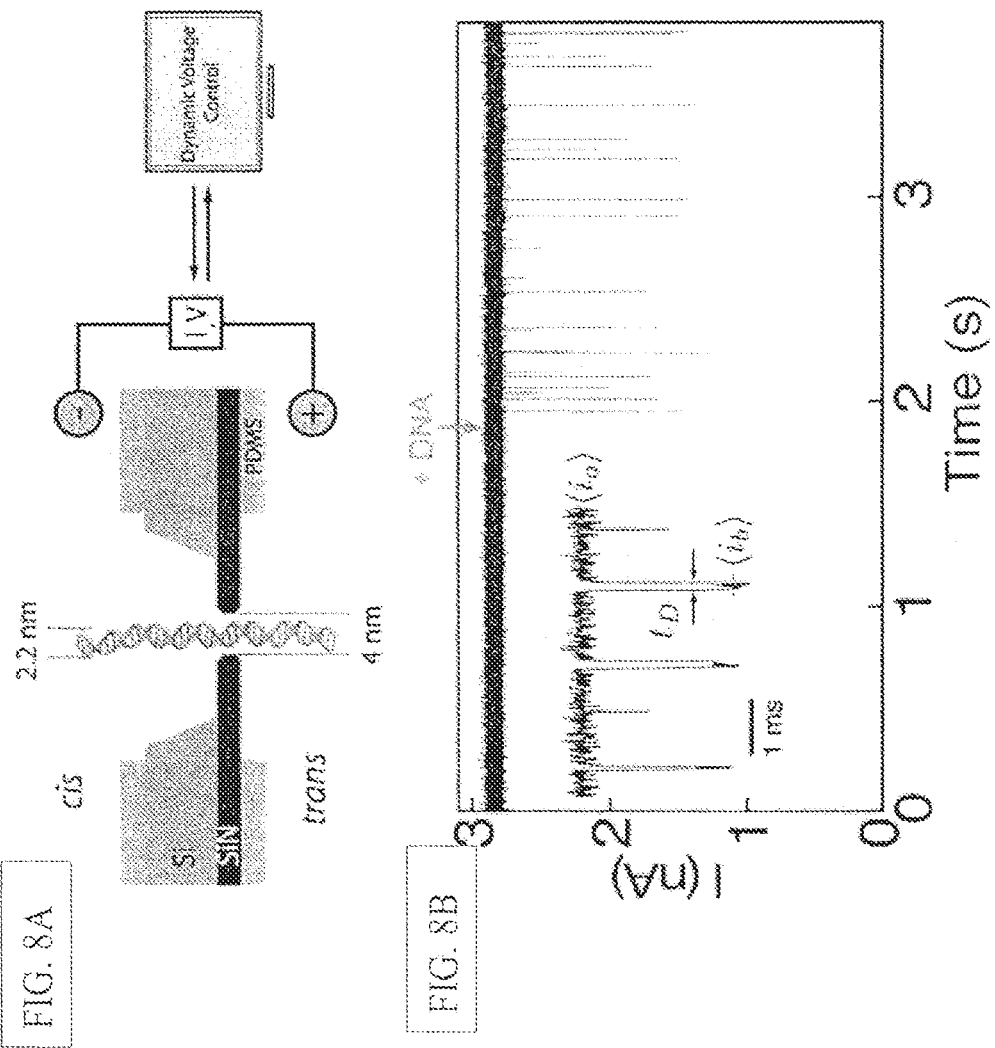

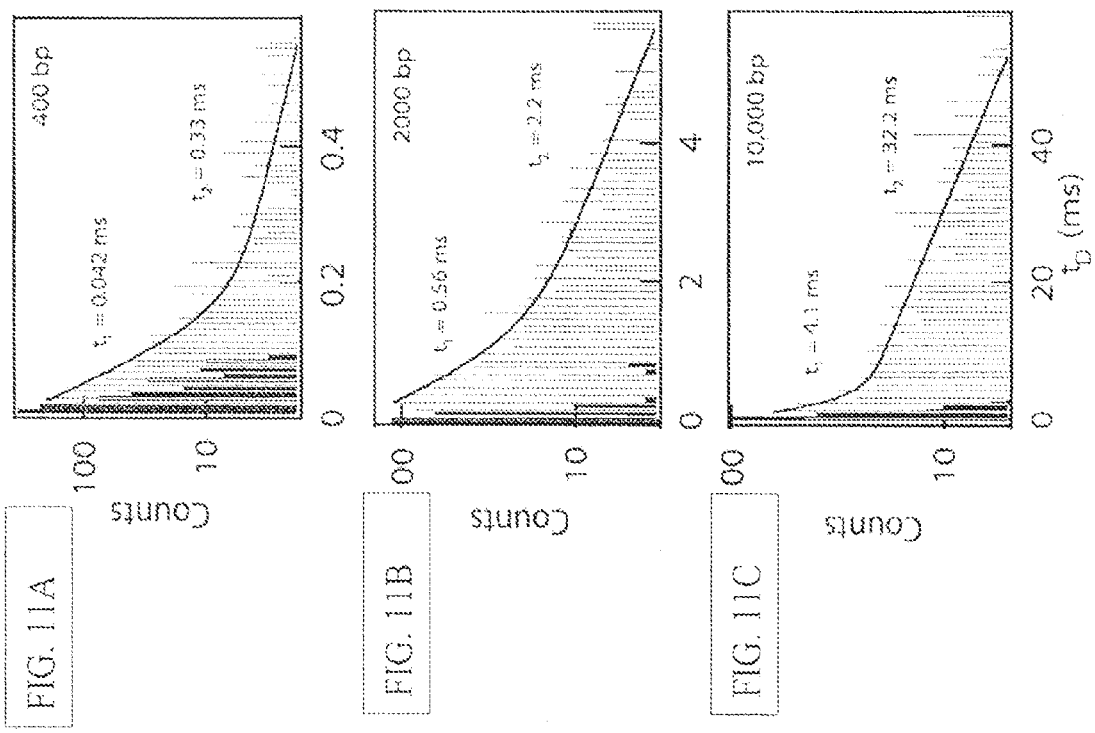

CHEMICAL FUNCTIONALIZATION OF SOLID-STATE NANOPORES AND NANOPORE ARRAYS AND APPLICATIONS THEREOF

CROSS REFERENCE TO RELATED APPLICATIONS

This application is a divisional of U.S. application Ser. No. 12/599,440, filed Nov. 18, 2010, which is a national stage entry of PCT/US2008/063066, filed May 8, 2008, which claims the benefit of priority under 35 U.S.C. § 119(e) to each of the following applications: U.S. Provisional Appl. No. 60/928,160, filed May 8, 2007, entitled Chemical Functionalization of Solid-State Nanopores and Nanopore Arrays and Applications Thereof; U.S. Provisional Appl. No. 60/928,260, filed May 8, 2007, entitled Chemical Functionalization of Solid-State Nanopores and Nanopore Arrays and Applications Thereof; and U.S. Provisional Appl. No. 60/928,158, filed May 8, 2007, entitled Chemical Functionalization of Solid-State Nanopores and Nanopore Arrays and Applications Thereof; the contents of which are hereby incorporated in their entireties.

This application is related to U.S. Provisional Patent Application No. TBD, filed on date even herewith, entitled Chemical Functionalization of Solid-State Nanopores and Nanopore Arrays and Applications Thereof, the entire contents of which are herein incorporated by reference.

This invention was made with Government Support under Contract No. PHY-0403891 awarded by the National Science Foundation. The Government has certain rights in the invention.

BACKGROUND

1. Technical Field

The present invention relates to chemical functionalization of solid-state nanopores and nanopore arrays, methods of forming chemically modified solid-state nanopores and applications thereof.

2. Discussion of Related Art

Nanopores, pores of nanometer dimensions in an electrically insulating membrane, have shown promise for use in a variety of sensing applications, including single molecule detectors. The nanopores used in such applications can be biological protein channels in a lipid bilayer or a pores in a solid-state membrane. Solid-state nanopores are generally made in silicon compound membranes, one of the most common being silicon nitride. Solid-stale nanopores can be manufactured with several techniques including ion-beam sculpting of silicon nitride and using a-beam lithography and wet etching in crystalline silicon followed by oxidation.

There also has been recent demonstration (Golovchenko's group in the Harvard Physics Department) of a reliable nano sculpting approach for making single nanopores of 1.5 nm in diameter in silicon-nitride solid-state membranes. In this approach, the processing steps employing focused ion beam lithography and low energy sputtering with feedback monitoring are highly reproducible and reliable. However, these nanopores are still too long (>10 nm) for use in measuring single nucleotides (see: J. Li, D Stein, C McMullan, D Branton, M. J. Aziz and J. A. Golovchenko; *Ion-Beam sculpting at nanometer length scales*, Nature 412, 166-169 (2001), the entire contents of which are herein incorporated by reference).

The use of nanopores in single-molecule detection employs a detection principle based on monitoring the ionic current of an electrolyte solution passing through the nanopore as a voltage is applied across the membrane. When the nanopore is of molecular dimensions, passage of molecules causes interruptions in the open pore current level. The temporal variation in current levels leads to a translocation event pulse. These detection methods are described at length in: Kasianowicz J J, Brandin E, Branton D. Deamer D W (1996) Characterization of individual polynucleotide molecules using a membrane channel. *Proc. Nat Acad Sci* 93:13770-13773; Akeson, M, Branton, D, Kasianowicz J, Brandin E and Deamer D, (1999) Biophys. J. 77: 3227-3233; Meller A, Nivon L, Brandin E, Golovchenko J, Branton D, (2000) *Proc Nat Acad Sci* 97: 1079-1084, all of which are herein incorporated by reference in their entireties.

Nanopore detection techniques have been used for biomolecule detection. For example, various nanopore sequencing methods have been proposed. In 1994, Bezrukov, Vodyanoy and Parsegian showed that one can use a biological nanopore as a Coulter counter to count individual molecules (*Counting polymers moving through a single ion channel*, Nature 370, 279-281 (1994) incorporated, herein, by reference. In 1996, Kasianowicz, Brandin, Branton and Deamer proposed an ambitious idea for ultrafast single-molecule sequencing of single-stranded DNA molecules using nanopore ionic conductance as a sensing mechanism (*Characterization of individual polynucleotide molecules using a membrane channel*, Proc. Nat. Acad Sci. USA 93 13770-13773 (1996), incorporated herein by reference). Since then, several groups have explored the potential of α-hemolysin protein pore as a possible candidate for achieving this objective. (See, for example: Akeson, M, Branton, D, Kasianowicz J, Brandin E, and Deamer D, (1999) Biophys. J. 77: 3227-3233; Meller A, Nivon L, Brandin E, Golovchenko J. Branton D, (2000) *Proc Nat Acad Sci* 97: 1079-1084; Braha, O.; Gu, L. Q.; Zhou, L.; Lu. X.; Cheley, S.; Bayley, H. *Nat. Biotech.* 2000; Meller A. Nivon L, and Branton, D. (2001) *Phys. Rev. Lett.* 86:3435-3438: Meller A. and Branton D. (2002) *Electrophoresis*, 23:2583-2591; Bates M, Burns M, and Meller A (2003) *Biophys. J.* 84:2366-2372; Zwolak M, Di Ventra M (2007). *Rev Mod Phys* 80:141-165, each of which is herein incorporated by reference in its entirety) The methods seek to effectively determine the order in which nucleotides occur on a DNA strand (or RNA). The theory behind nanopore sequencing concerns observed behavior when the nanopore is immersed in a conducting fluid and a potential (voltage) is applied across it. Under these conditions an electrical current that results from the conduction of ions through the nanopore can be observed. The amount of current which flows is sensitive to the size of the nanopore. When a biomolecule passes through the nanopore, it will typically create a change in the magnitude of the current flowing through the nanopore. Electronic sensing techniques are used to detect the ion current variations, thereby sensing the presence of the biomolecules.

U.S. Pat. No. 6,428,959, the entire contents of which are herein incorporated by reference, describes methods for determining the presence of double-stranded nucleic acids in a sample. In the methods described, nucleic acids present in a fluid sample are translocated through a nanopore, e.g., by application of an electric field to the fluid sample. The current amplitude through the nanopore is monitored during the translocation process and changes in the amplitude are related to the passage of single- or double-stranded molecules through the nanopore. Those methods find use in a variety of applications in which the detection of she presence of double-stranded nucleic acids in a sample is desired.

There are numerous challenges to develop effective nanopore detection techniques. Control of nanopore surface characteristics presents an obstacle to nanopore use in detection applications. Without refused control over the nanopore characteristics, nanopore detection apparatus cannot be constructed to be selectively sensitive to desired molecules or environmental alterations. It would be desirable to provide solid-state nanopores wish surface characteristics that can be selectively modified to enable specific uses in detection and sensing applications.

SUMMARY

The present invention relates to chemical functionalization of solid-state nanopores and nanopore arrays, methods of forming chemically modified solid-state nanopores and applications thereof.

According to one embodiment of the invention, a coated nanopore includes a solid-state insulating membrane having a thickness between approximately 5 nanometers and approximately 100 nanometers. The membrane has an aperture with at least one surface with chemical coating disposed on the surface. The chemical coating modifies at least one surface characteristic of the aperture.

Under another aspect of the invention, the solid state insulating membrane includes a silicon nitride material.

Under another aspect of the invention, the chemical coating disposed on the surface of the aperture includes a layer substantially conformal to the surface of the aperture.

Under another aspect of the invention, the chemical coating has a selected thickness and distribution.

Under another aspect of the invention, the selected thickness may be less than or equal to approximately 2.5 nanometers.

Under another aspect of the invention, the surface characteristic includes at least one of concavity, surface charge, polarity, pH sensitivity, hydrophobicity, and chemical functionality.

Under another aspect of the invention, the chemical coating includes an organic monolayer coating.

Under another aspect of the invention, the chemical coating includes one of an epoxy, a methoxyethylene glycol, an amine, a carboxylic acid, and an aldehyde.

Under another aspect of the invention, the chemical coating includes a methoxyethelyne glycol-terminated silane monolayer.

Under another aspect of the invention, the organic monolayer coating includes a reactive monolayer forming covalent bonds with the surface of the aperture.

Under another aspect of the invention, the chemical coating includes a substantially uniform layer of chain molecules including organosilanes.

According to another embodiment of the invention, an electrically-addressable nanopore array includes a solid-state insulating membrane having a thickness between approximately 5 nanometers and approximately 100 nanometers. A plurality of nanopores are formed in the membrane, each nanopore having a surface. A plurality of electrodes are disposed adjacent to the plurality of nanopores. A chemical coating is disposed on the surface of each nanopore, the chemical coating modifying a surface characteristic of the nanopore. The plurality of electrodes selectively address each nanopore in the array to detect changes in electrical stimulus at each nanopore in the array.

Under another aspect of the invention, the chemical coating disposed on the surface of each nanopore is selected to detect ions.

According to another embodiment of the invention, an optically-addressable nanopore array includes a solid-state insulating membrane having a thickness between approximately 5 nanometers and approximately 100 nanometers. A plurality of nanopores are formed in the membrane, each nanopore having a surface. A plurality of electrodes are disposed adjacent to the plurality of nanopores. A chemical coating is disposed on the surface of each nanopore, the chemical coating modifying a surface characteristic of the nanopore. The plurality of optical sensors selectively address each nanopore in the array to detect energy emission variations at each nanopore in the array.

Under another aspect of the invention, the chemical coating disposed on the surface of each nanopore includes a pH-sensitive dye such as a fluorophore.

According to another embodiment of the invention, a method of making a coated solid-state nanopore includes fabricating a nanoscale aperture in a solid-state substrate, cleaning a surface of the aperture, and chemically modifying the surface of the aperture to fabricate a chemical coating. The chemical coating is substantially conformally disposed on the surface. The coated solid-state nanopore is fabricated with a chemical coating of a selected composition and distribution.

Under another aspect of the invention, chemically modifying the surface of the aperture comprises a sequence of chemical coating steps.

Under another aspect of the invention, the sequence of chemical coating steps includes for each coating step, immersing in solution, drying, and heating the solid-state substrate.

Under another aspect of the invention, each coating step includes an ex situ chemical process.

Under another aspect of the invention, the sequence of chemical coating steps includes, for each coating step, exposing the aperture to a sequence of chemical solutions, each chemical solution in the sequence having a selected composition.

Under another aspect of the invention, chemically modifying the surface of the aperture includes an in situ coating process in which variations in current adjacent to the aperture are monitored while the aperture surface is chemically modified.

Under another aspect of the invention, the nanoscale aperture includes an aperture having a diameter less than or equal to approximately 10 nanometers.

Under another aspect of the invention, cleaning the surface of the aperture includes treating the surface with a piranha solution.

Under another aspect of the invention, the method further includes characterizing the coating to detect the selected concentration and distribution.

Under another aspect of the invention, chemically modifying the surface includes coating with at least one of epoxy, methoxyethylene glycol, amine, carboxylic acid, and aldehyde.

Under another aspect of the invention, chemically modifying the surface includes coating with at least one of glycidyloxypropyltrimethoxysilane, methoxyethoxyundecyltrichlorosilane, 3-aminopropyltrimemoxysilane, adipoyl chloride, 1,4-diaminobutane, and glutaraldehyde.

According to another embodiment of the invention, a method for characterizing an analyte includes forming a nanopore in a solid-state membrane having a thickness between approximately 5 nanometers and approximately 100 nanometers, chemically modifying a surface of the nanopore, receiving the analyte through the nanopore, and detecting variations in current adjacent to the nanopore. The variations in current correspond to interactions between the analyte and nanopore surface.

Under another aspect of the invention, chemically modifying the surface of the nanopore comprises tuning the interaction between the analyte and the nanopore.

Under another aspect of the invention, chemically modifying the surface of the nanopore comprises coating the nanopore with a substantially uniform layer of short chain molecules including organosilanes.

Under another aspect of the invention, the analyte includes a biopolymer.

Under another aspect of the invention, the biopolymer includes one of single-stranded DNA, double-stranded DNA, RNA, and a nucleic acid polypeptide.

Under another aspect of the invention, chemically modifying the surface of the nanopore includes providing a chemical coating to substantially slow DNA translocation.

Under another aspect of the invention, chemically modifying the surface of the nanopore includes providing a chemical coating to substantially prevent sticking between the biopolymer and the surface of the nanopore.

Under another aspect of the invention, the nanopore dimensions are selected to substantially slow DNA translocation.

Under another aspect of the invention, detecting variations in current includes detecting variations in local ion current with electrodes disposed adjacent to the nanopore.

Under another aspect of the invention, detecting variations in local ion current comprises detecting an open nanopore current and a blocked nanopore current, the blocked nanopore current varying with respect to analyte-coated nanopore interaction characteristics.

Under another aspect of the invention, the analyte includes a DNA and the blocked nanopore current varies with respect to DNA length.

According to another embodiment of the invention, a method of identifying a biomolecule includes modifying a surface of a nanopore with a chemical coating, immobilizing the biomolecule on the surface of the nanopore, exposing the nanopore to a chemical environment, and detecting variations in current adjacent to the nanopore. The variations in current correspond to interactions between the biomolecule and the chemical environment. Selected interactions identify the biomolecule.

Under another aspect of the invention, immobilizing the biomolecule includes chemically grafting the molecule in a central portion of the nanopore.

Under another aspect of the invention, modifying the surface with the chemical coating includes providing a glutaraldehyde-functionalized nanopore.

Under another aspect of the invention, modifying the surface with the chemical coating includes providing an organic monolayer coating.

Under another aspect of the invention, the organic monolayer coating includes a reactive monolayer forming covalent bonds with the surface of the aperture.

Under another aspect of the invention, exposing the nanopore to a chemical environment includes providing a chemical gradient having a first chemical environment on a first side of the nanopore and a second chemical environment on a second side of the nanopore.

Under another aspect of the invention, immobilizing the biomolecule includes providing a selective transport path between the first and second chemical environments.

Under another aspect of the invention, the molecule includes a beta-pore forming protein including a single α-hemolysin channel an a α-hemolysin channel mutant. The chemical coating comprises a methoxyethelyne glycol-terminated silane monolayer.

Under another aspect of the invention, the chemical coating comprises an aldehyde reactive terminal layer.

According to another aspect of the invention, a method of sensing a chemical environmental includes forming a nanopore in a solid-state membrane, the membrane having an thickness between approximately 5 nanometers and approximately 100 nanometers. The method includes chemically modifying a surface of the nanopore, exposing the nanopore to a chemical environment, applying a voltage to at least a portion of the chemical environment in proximity to the membrane, and optically probing the membrane to detect energy emission variations. Energy emission variations correspond to interactions between the chemical environment and the surface of the nanopore.

Under another aspect of the invention, chemically modifying the surface of the nanopore includes coating the surface with a pH-sensitive dye.

Under another aspect of the invention, the pH-sensitive dye includes one of a fluorophore and a protein modulating group.

Under another aspect of the invention, variations in florescent intensity are detected such that variations in florescent intensity correspond to variations in the chemical environment.

Under another aspect of the invention, exposing the nanopore to a chemical environment includes providing a chemical gradient having a first chemical environment on a first side of the membrane and a second chemical environment on a second side of the membrane.

According to another embodiment of the invention, a method of sensing a chemical environmental includes forming a nanopore in a solid-state membrane, the membrane having an thickness between approximately 5 nanometers and approximately 100 nanometers. The method further includes chemically modifying a surface of the nanopore, exposing the nanopore to a chemical environment, applying a voltage to at least a portion of the chemical environment in proximity to the membrane, and detecting variations in current adjacent to the nanopore. The variations in current correspond to interactions between the chemical environment and nanopore surface.

Under another aspect of the invention, chemically modifying the surface of the nanopore includes coating the surface with a pH-sensitive molecule.

Under another aspect of the invention, exposing the nanopore to a chemical environment includes providing a chemical gradient having a first chemical environment on a first side of the membrane and a second chemical environment on a second side of the membrane.

Under another aspect of the invention, chemically modifying the surface of the nanopore includes coating the surface with a selected ion-sensitive compound.

BRIEF DESCRIPTION OF THE DRAWINGS

In the Drawings:

FIG. 5A illustrates current-time traces for the addition of a compound with functional silane monolayers to the cis chamber of a bare 10 nm (I) and amine-coated 12 nm nanopore (II), according to various embodiments of the invention.

FIG. 5B illustrates a plot showing normalized change in the ion current of nanopores coated with an aminosilane upon the addition of gluteraldehyde to selected concentrations in the cis-chamber, according to various embodiments of the invention.

FIG. 5C in the inset illustrates time constant ($\tau$) fitting results to first-order adsorption kinetics for the selected concentrations shown in FIG. 5B.

FIG. 7A illustrates a schematic representation of the translocation of biopolymers through uncoated silicon nitride nanopores, according to one embodiment of the invention.

FIG. 7B illustrates a schematic representation of the translocation of biopolymers through polymerscan coated nanopores, according to one embodiment of the invention.

FIG. 7C illustrates a schematic representation of protein immobilization inside a selectively coated nanopore, according to one embodiment of the invention.

FIG. 7D illustrates a schematic representation of protein immobilization inside a selectively coated nanopore, according to one embodiment of the invention.

FIG. 8A illustrates a schematic view of a solid state nanopore device for probing DNA translocation dynamics, according to one embodiment of the invention.

FIG. 8B shows a plot of a typical ion current trace for a solid state nanopore device, according to one embodiment of the invention.

FIG. 11 A-C illustrate plots of dwell-time distributions for different DNA lengths, according to various embodiments of the invention.

DETAILED DESCRIPTION

Introduction

Figure 1:
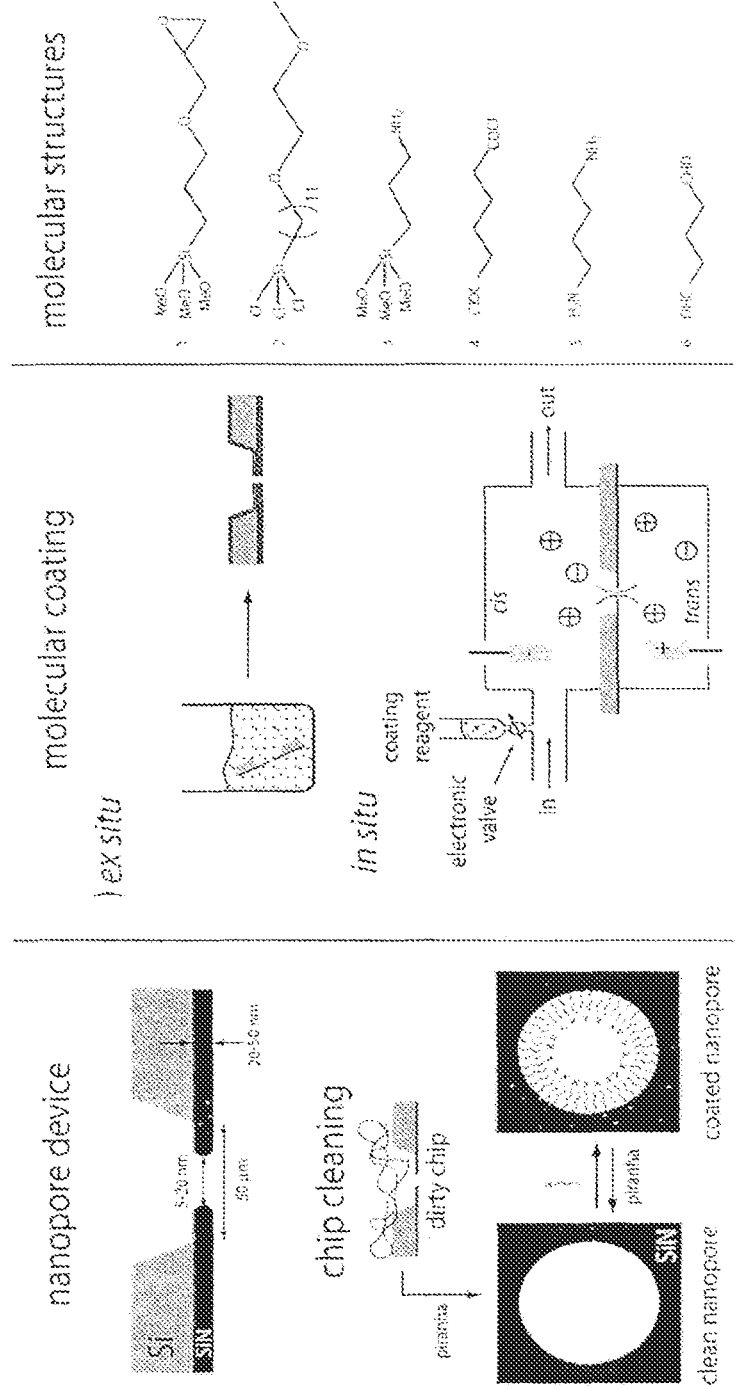
FIG. 1A illustrates a schematic picture of the nanopore device and chip cleaning, according to various embodiments of the invention.
FIG. 1B illustrates two schemes for coating nanopores, the ex situ method and the in situ method, respectively, according to various embodiments of the invention.
FIG. 1C illustrates structures of the molecules used for various coatings.

The present invention features devices and systems embodying one or more solid-state nanopores that can be used in a variety of sensing and detection applications. The chemical modification of nanopores in thin, solid-state membranes through novel coating methods enables these applications. These applications include the characterization of single molecules, sequencing of DNA or RNA, pH sensing in an environment and, in certain cases, chemical transport. Nanoscale-control over the surface properties of nanopores can govern the nanopore's interactions with various substances and environments. The present application details chemical functionalization of solid-state nanopores and applications of coated nanopores.

Techniques for the chemical functionalization of nanopores, described below, have significant implications for the usefulness of thin, solid-state membranes in sensing and detection applications. These techniques enable the integration of nanopore sensing apparatus in a variety of systems. In this specification, thin, solid-state membranes should at least be understood to mean a thin layer of material having a thickness ranging between approximately 5 nanometers and approximately 100 nanometers and comprising an insulating (or semiconducting) inorganic compound, for example a Si-based material such as silicon oxide, silicon nitride, a mixture thereof, or various materials having a highly viscous, glasslike behavior. Solid-state should be understood to encompass that group of materials typically defined as solid-stale by the semiconductor industry with regard to various electronics applications. Nanopores should be understood to entail apertures of nanoscale dimensions formed in a membrane. In this specification, the aperture refers to a passage in a particular membrane, open to two opposite sides of the membrane. The surface of the aperture should be understood to mean at least the exposed surface of the membrane forming axially-oriented walls of the aperture, in this application, nanometer-scale indicates linear dimensions between 0 and approximately 1,000 to 10,000 nanometers (nm). In this specification, interactions outside the nanopore will be referred to as "DNA/membrane interactions" to distinguish them from "DNA/Nanopore interactions" inside the nanopore, although the chemical nature of the two forms of interactions may be similar.

The present invention relates to novel methods for chemically modifying solid-state nanopore surfaces, as well as the characterization of chemically-modified nanopores. From a technical point of view, the chemical modification of highly concave surfaces, such as those found in nanopores, is quite challenging. With curvatures approaching the length scale of the molecules (~1 nm), nanopore surfaces are far more difficult to coat than planar surfaces. The difficulty can be attributed to a variety of sources. First, molecular arrangement on concave surfaces is, to date, unknown, in contrast to the well-studied order on planar surfaces. Second, the number of molecules that can be bound to the area of a single nanopore is low (approximately 100-1000), suggesting poor layer quality. The present methods overcome these challenges, demonstrating stable nanopore coating.

Stable nanopore coating techniques (ex situ and in situ) provide useful applications of chemically-modified nanopores. Ex situ chemical coating is a technique suitable for coating large-dimensioned solid-state nanopores (e.g. greater than approximately 10 nm diameter) characterized by an incremental process wherein sequential coatings are applied in stages. Each stage is typically separated by an imaging step to detect nanopore modification. In situ chemical coating is a technique for coating solid-state nanopores characterized by monitoring the chemical functionalization process as it proceeds and preventing small-dimensioned nanopores (less than approximately 10 nm in diameter) from clogging with the coating compound.

Nanopores are small holes (approximately 1-100 nm diameter) in a partition ("membrane") whose thickness is of similar order. The membrane divides a volume into two separate compartments, each of which may contain different types and/or concentrations of analyses. One or more pore(s) is the only passage between these two compartments. When electrodes are placed in each compartment and a voltage is applied, an electric field develops across the nanopore. The applied electric field acts as a force on charged molecules and ions inside the nanopore. In the case of nanopore-immobilized molecules (e.g., enzymes), this electric field may also induce structural changes, which may in turn modulate their activity. Therefore, immobilization of proteins, enzymes or other forms of chemical functionalization at the nanopore juncture provides possibilities which have not been achieved by the immobilization of molecules on planar surfaces. Several applications, which are based on this property, are envisioned and described in detail below.

Nanopores have emerged in recent years as versatile single-molecule detectors. The sensing principle is based on transient interruptions in the ion-current of an electrolyte, induced by the entry, transport, and exit of a particular analyte from the pore. A distinguishing feature of nanopores is that they can be used to analyze not only small molecules, but also long biopolymers, such as DNA and RNA, with resolution on the order of the nanopore length (several nm). A well-studied system involves the lipid-embedded α-hemolysin (α-HL) protein pore, which can accommodate various types of biopolymers. α-HL has been used extensively to discriminate between DNA and RNA sequences, to study DNA unzipping kinetics, orientation of entry, DNA-protein interactions, and peptide transport. An important outcome of these studies has been the realization that threaded biopolymer dynamics is governed by the biopolymer's interactions with the nanopore walls. This notion has been utilized for the detection of small molecules, metal-ions, and the discrimination of enantiomer drugs, by employing molecular biology methods to modify the α-HL nanopore. However, the range of sensing applications using α-HL is limited by its fixed dimensions and the delicate nature of a lipid membrane.

To expand the realm of nanopore sensing, synthetic nanopores have recently been introduced using a variety of materials, such as polymers, glass, and thin solid-state membranes. (See: PCT Patent Pub. No. WO2004/078640A 1. Methods and apparatus for controlled manufacturing of nanometer-scale apertures, filed Mar. 5, 2003 by Storm et al., which is herein incorporated by reference in its entirety.) Such nanopores have demonstrated utility for sensing single-stranded and double-stranded DNA, ions, macromolecules, and proteins. (See, for example, Fologea, Gershow, Ledden, McNabb, Golovchenko and Li, *Detecting single stranded DNA with a solid state nanopore*. NanoLetters Vol. 5, No. 10 1905-1909 (2005), herein incorporated by reference in its entirety.) Nanopores incorporated in thin (~10 nm) solid-state inorganic membranes are highly promising materials, since the nanopore volume can be reduced to a few nm in all dimensions, on par with biological membrane channels. In addition, the planar geometry permits high-resolution fabrication and characterization using the transmission electron microscope (TEM), as exemplified by sub-nm size control for nanopores down to 1 nm diameters. Further, the fabrication of high-density nanopore arrays is possible, setting the stage for high-throughput biomolecular analysis, in particular ultra-fast DNA sequencing.

Coated nanopores in thin (~10 nm) solid-state inorganic membranes enable a broad range of nanopore sensing applications. The coating techniques described below permit highly refuted control over the surface characteristics of each nanopore. Because a variety of coatings may be used, as suitable for each sensing application, the detection mechanism is not limited to electrical detection only. Optical detection mechanisms may be preferable for certain embodiments. The present technology is highly scalable, with both optically- and electrically-addressable nanopore array assemblies enabling detection over a surface area.

Electrical detection mechanisms rely on ion current sensing. Ion current sensing for individual nanopores and nanopore arrays typically uses a potassium chloride or other electrolyte solution (salt solution). A nanopore membrane separates two reservoirs of ionic solution. When voltage is applied across the two reservoirs, the potential drop almost entirely occurs at the nanopore. Therefore the ionic conductance or resistance between the two reservoirs is also the conductance or resistance of the nanopore. The nanopore conductance transiently drops when a molecule (e.g. DNA) enters and exits the nanopore, allowing its detection. By analyzing the transient conductance spikes, the properties of biopolymers (size, charge, structure) can be investigated. This detection scheme can be parallelized using an array of nanopores with individual electrodes situated at each chamber. The individual electrodes are then uniquely addressable using techniques well-known in the semiconductor industry.

Optical defection schemes are also effective in chemically-modified nanopore sensors. Nanopore surfaces may be chemically functionalized with fluorescent molecules. In this mode of sensing, a voltage is used to drive molecules through the nanopores, while a microscope is used to sense light output from each nanopore in the membrane. The nanopore (or array of nanopores) is assembled in a cell containing a transparent window allowing optical probing of the membrane, while fluorescent molecules are detected as they occupy the pore. In various applications, creating chemically-modified nanopores entails introducing fluorescent molecules only at the pore (as opposed to over an area of the membrane) by performing two complementary reactions at opposite sides of the membrane. The size of each pore in the array can be either uniform or varying (for example, a gradient of size and shape across a portion of the membrane). The location of each pore in the array is specified during the fabrication process so that each pore has a known location. Alternately, the pores can be optically detected using fluorescent molecules. The spacing between pores is chosen so that optical probing would have sufficient resolution to address each pore (e.g approximately 500 nm spacing between adjacent pores). The apparatus for optical sensing is highly effective and used in several applications, detailed below.

Methods of Coating Solid-State Nanopores

Nanopores are extremely sensitive single-molecule sensors. Recently, electron beams have been used to fabricate synthetic nanopores in thin solid-state membranes with sub-nanometer resolution. A new class of chemically modified nanopore sensors are disclosed. Two approaches for monolayer coating of nanopores, described in detail below, include: (1) self-assembly from solution, in which nanopores ~10 nm diameter can be reproducibly coated, and (2) self-assembly under voltage-driven electrolyte flow, in which 5 nm nanopores are coated. An extensive characterization of coated nanopores, their stability, reactivity, and pH response is described below.

Nanoscale control over the surface properties of nanopores can govern its interactions with various analytes, resulting in "smart" nanopore sensors. Various approaches for nanopore functionalization have been reported, from deposition of metals, oxides, to various organic modifications. However, the resulting nanopore structure often gains significant thickness, and in some cases the morphology is unknown, due to unavailability of imaging methods. In particular, molecular coating of solid-state nanopores approaching the nm scale in all dimensions has not been reported to date. Robust procedures for chemical modification of nanopores of sizes 5-20 nm fabricated in thin SiN membranes are provided. Self-assembly methods are employed to control the chemical and physical properties of a single nanopore, such as its charge, polarity, pH sensitivity, etc. Reproducible coating of nanopores as small as 5 nm are described that demonstrate surface modification, fast reaction kinetics, and pH responsiveness. Dressing an inorganic pore surface with a variety of organic coatings not only makes it more biologically friendly, but further allows control of surface charge, hydrophobicity, and chemical functionality. An ultra-sensitive single nanopore pH sensor operating at physiological ionic strengths is described.

An exemplary solid-state nanopore device is depicted in FIG. 1A (left panel) which provides schematic picture of the nanopore device. Piranha solution is used to clean the nanopore surfaces before coating with organosilanes, as well as to "uncoat" the nanopores. FIG. 1B (middle panel) shows a depiction of two schemes for coating nanopores. In the ex situ method, the activated nanopore is simply immersed in silane solution, followed by cleaning steps (not shown). In the in situ method, the nanopore device is assembled in a two-chamber cell and a voltage is applied across it, driving supporting electrolyte through the pore during the silane deposition process. FIG. 1C (right panel) shows structures of the molecules used for various coatings. Molecules 1-3, as depicted in FIG. 1C, are organosilanes, while 4-6 are used in further reactions with functional silane monolayers.

The SiN membrane surface contains a native oxide layer, which is used here for monolayer self assembly of organosilanes. Prior to coating, piranha treatment is used for removal of contaminants and surface activation. Further, the coating procedures are reversible: piranha treatment can be used to completely remove the organic coatings and regenerate the clean nanopore surface. The middle panel, FIG. 1B, shows two alternative molecular coating approaches: a) Ex situ assembly, in which the organic coating is performed by immersion of the nanopore chip into the deposition solution, and b) In situ assembly, in which organic molecules are allowed to react with the nanopore surface under driven electrolyte flow. There are different advantages to each of the ex situ and in situ coating method, depending on the embodiment. The ex situ coating method entails a simpler process whereas the in situ assembly, for example, is capable of coating smaller nanopores without clogging, down to approximately 5 nm. Both ex situ and in situ chemical coating methods may be used for nanopore fictionalization using self-assembly of organosilane molecules. A number of analytical methods have been employed to clearly demonstrate: A) monolayer coating of various chemical groups inside >10 nm pores fabricated in SiN membranes, and B) ion-current through the coated nanopores closely correlates with the coating thickness. In situ measurements may be used to probe the coating kinetics in real time.

On the right panel, FIG. 1C, the molecules used for coating the nanopores are shown. Films designated with a "+" sign may be prepared by multiple reaction steps. Several coatings with common functional groups are used: Epoxy (1), methoxyethylene glycol "PEG"-type) (2), amine (3, 3+5), carboxylic acid (3+4), and aldehyde (6). Molecules 1-3 are organosilanes, which directly self-assemble on the nanopore surface to form functional monolayers. Molecules 4 and 6 were used to convert amine-coated surfaces to carboxylic acid and aldehydes, respectively. Molecule 5 was used in further reaction with the 3+4 surface to generate a thicker amine coating.

Other coating materials may also be employed, depending on the particular application. For example, various silanes include a first moiety which binds to the surface of a semiconductor membrane and a second moiety which binds to various tethered molecules. These silanes include, without limitation, 3-glycidoxypropyltrialkoxysilanes with C1-6 alkoxy groups, trialkoxy(oxiranylalkyl)silanes with C2-12 alkyl groups and C1-6 alkoxy groups, 2-(1,2-epoxycyclohexyl)ethyltrialkoxysilane with C1-6 alkoxy groups, 3-butenyl trialkoxysilanes with C1-6 alkoxy groups, alkenyltrialkoxysilanes with C2-12 alkenyl groups and C1-6 alkoxy groups, tris[(1-methylethenyl)oxy]3-oxiranylalkyl silanes with C2-12 alkyl groups, [5-(3,3-dimethyloxiranyl)-3-methyl-2-pentenyl]trialkoxysilane with C1-6 alkoxy groups, (2,3-oxiranediyldi-2,1-ethanediyl)bis-triethoxysilane, trialkoxyl[2-(3-methyloxiranyl)alkyl]silane with C1-6 alkoxy groups and C2-12 alkyl groups, trimethoxy[2-[3-(17,17,17-trifluoroheptadecyl)oxiranyl]ethyl]silane, tributoxy[3-[3-(chloromethyl)oxiranyl]-2-methylpropyl]silane, any alkylsilane where the alkyl groups have a varying length between 3 and 30 carbons, and combinations thereof. Silanes can be coupled to the semiconductor membrane according to a silanization reaction scheme (see, for example, PCT Publication Nos. WO/2006/0278580 and WO/2002/068957, the contents of which are hereby incorporated by reference in their entireties).

By controlling the properties of the film used for coating the nanopores, the characteristics of the nanopore may be refined for a variety of applications. The ex situ method for chemical functionalization of nanopore surfaces includes a sequence of chemical coating steps alternated with measurements to detect coating thickness, composition and surface characteristics. Film thickness, roughness and chemical composition of the different films on planar SiN substrates may be determined through ellipsometry, non-contact atomic force microscopy (AFM) and X-ray photoelectric spectroscopy (XPS). Table 1 displays data comparing the ellipsometric thickness, δ, with the calculated thickness based on molecular models. Measured thicknesses are in agreement with calculated values for films 1-3, indicating she formation of homogeneous monolayers on the SiN substrate. The increase in film thickness upon the addition of 4 or 6 suggests that the amine group remains reactive on the surface. Further, reaction of the terminal carbonyl chloride 3+4 with diamine 5 was successful. AFM characterization on these films yielded RMS roughness values in the range 0.4-0.7 nm, similar to uncoated SiN (0.58 nm), implying a homogeneous film distribution.

TABLE 1

Characterization of the molecular films on SiN substrates using ellipsometry.

| Film | $n_f$[†] @633 nm | Ellipsometry δ (nm) | Model thickness[‡] (nm) |
|---|---|---|---|
| 1 | 1.43 | 1.4 ± 0.1 | 1.1 |
| 2 | 1.46 | 2.5 ± 0.2 | 2.2 |
| 3 | 1.50 | 0.6 ± 0.1 | 0.7 |
| 3 + 4 | 1.50 | 1.2 ± 0.2 | 1.4 |
| 3 + 4 + 5 | 1.50 | 1.7 ± 0.2 | 2.1 |
| 3 + 6 | 1.50 | 1.1 ± 0.2 | 1.3 |

[†]Based on bulk refractive index values.
[‡]Calculated from molecular models (CS Chem3D), assuming upright orientation on the surface.

Figure 2:
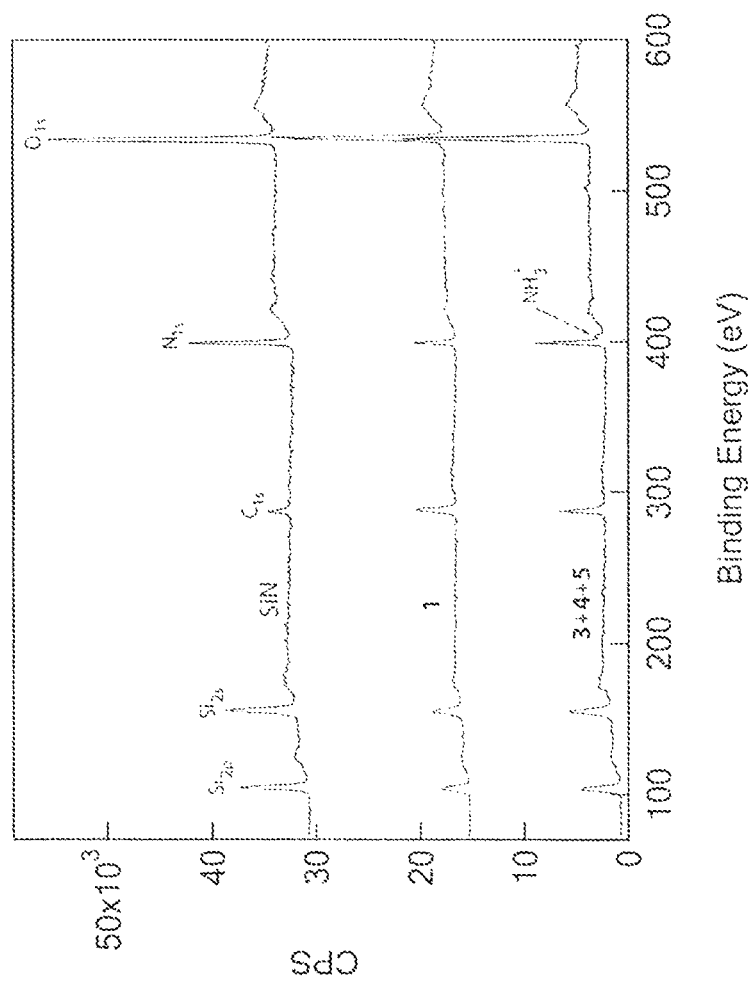
FIG. 2 illustrates XPS spectra of bare SiN films on Si (top), and the same substrates after coating with 1 (middle) and 3+4+5 (bottom), according to one embodiment of the invention.

XPS measurements were performed to validate the chemical identity of the coated films. FIG. 2 shows XPS spectra of bare (piranha-treated) SiN films on Si (top), and the same substrates after coating with 1 (middle) and 3+4+5 (bottom). The SiN exhibits strong signals for Si, N, and O, as well as a residual C signal, attributed to contamination. Following coating with 1 (middle curve), a reduction of signals for Si, O, and N, coupled with an increase of the C signal were observed. The amino-terminated film (3+4+5) exhibits a second N peak at 402 eV (see arrow), corresponding to a protonated amine state on the film ($NH_3^+$). A peak at 402 eV is attributed to the presence of ammonium ions in the film 3+4+5. The middle and the top curves were shifted by $15·10^3$ cps and $30·10^3$ cps respectively.

TABLE 2

Ion-conductance at 1M KCl, pH 8.5, for bare and coated nanopores (n = number of trials).

| Coating | $D_{bare}$ (nm) | $G_{bare}$ (nS) | $G_{coated}$ (nS) | $<d_{eff}>$ (nm)[†] | d (nm)[‡] |
|---|---|---|---|---|---|
| 1 | 13 (n = 2) | 75 ± 4 | 35 ± 4 | 9.5 | 10 |
|   | 10 (n = 5) | 34 ± 4 | 20 ± 5 | 7 | 7 |
| 2 | 15 (n = 2) | 120 ± 5 | 26 ± 3 | 9 | 10 |
|   | 10 (n = 2) | 34 ± 4 | 13 ± 4 | 6 | 6 |
| 3 | 14 (n = 2) | 100 ± 5 | 55 ± 8 | 12 | 12.5 |
|   | 12 (n = 10) | 65 ± 4 | 45 ± 5 | 11 | 10.5 |
| 3 + 4 + 5 | 25 (n = 1) | 250 | 110 | 18 | 21 |
|   | 10 (n = 1) | 31 | 9 | 5 | 6 |
| 3 + 6 | 12 (n = 10) | 65 ± 4 | 29 ± 7 | 9 | 9.5 |
|   | 10 (n = 1) | 33 | 8 | 5 | 7.5 |

[†]Average error in all values is ±10%.
[‡]Based on the ellipsometry thickness (see text).

The coating of highly concave surfaces in a confined volume is considerably different from coating of flat surfaces described above. Not only do the concave surfaces induce a different molecular packing, the highly confined volume of the nanopore may alter the adsorption kinetics. Furthermore, the characterization techniques described above cannot be used to probe coating inside a nanopore. On the other hand, the ion flux through the nanopores should be extremely sensitive to the nanopore coating thickness, since the ionic conductance (G) depends quadratically, to a first approximation, on the pore diameter, d. A series of ion-conductance measurements for uncoated and coated pores using nanopores with diameters in the range 10-25 nm validates this (Table 2). G was measured for each chip before and after the coating procedure and estimated the effective diameter, $d_{eff}$, based on the G values. These numbers were compared with the model coated nanopore size, $d'=d_{bare}-2\delta$, where $d_{bare}$ is the TEM measured diameter of the uncoated pore, and δ is the coating thickness measured by ellipsometry. An agreement between $d_{eff}$ and d' indicates that nanopore coating thickness is commensurate with surface coating thickness. As seen in Table 2, the effective nanopore sizes agree very well with the model size for all the coating types used, supporting the formation of monolayers with the expected thickness inside the nanopores. A reduction in G may also be attributed to an increase of the membrane thickness. However, only a negligible contribution is expected from this: on the 50 nm thick SiN membrane used in these measurements, the thickest coating (2.5 nm) should increase the membrane thickness by 10% (5 nm), and in turn should decrease G by 10% or less. In contrast, roughly an 80% decrease in G for this coating was observed, implying that the reduction in G is primarily due to coating inside the nanopore.

Figure 3B:
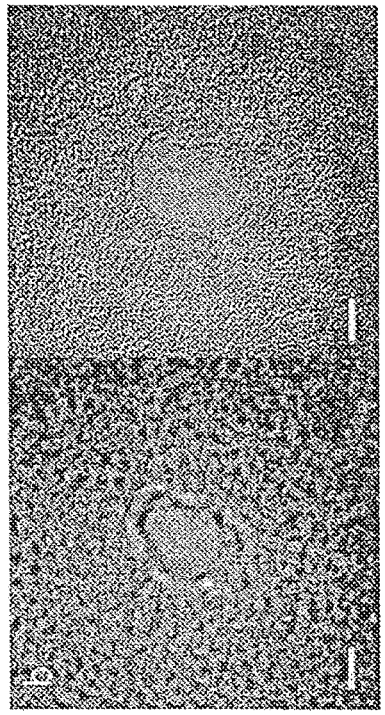
FIG. 3B illustrates on the Left: a TEM image of a 10 nm nanopore following coating with various coatings, and on the Right: a TEM image of the same pore after irradiation, according to one embodiment of the invention.
Figure 3A:
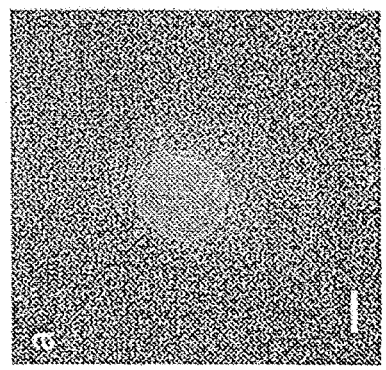
FIG. 3A illustrates bright-field TEM images of a 10 nm nanopore following cleaning with piranha solution, according to one embodiment of the invention.

Nanopore coating is further supported by high resolution TEM imaging. FIG. 3A illustrates a bright-field TEM images of a 10 nm nanopore following cleaning with piranha solution. FIG. 3B (left) illustrates a TEM image of a 10 nm nanopore following coating with compounds 3+4+5. FIG. 3B (right) illustrates a TEM image of the same pore after 30 s irradiation under low e-beam dose, during which the organic layer appears to have been removed. The scale bar in all images is 5 nm.

FIG. 33 displays a similar 10 nm pore after coating with the 1.7 nm thick 3+4+5 layer. Several marked differences appear: First, the coated surface displays larger grains. Second, the nanopore boundary appears dull, as opposed to the sharp SiN/pore boundary in the unmodified nanopore. The nanopore interior in the TEM image reveals an uneven grayish decoration (indicated by an arrow), attributed to coating. This layer is clearly in focus, marked by the sharp boundary between the coating and vacuum. The maximum estimated coating thickness is ~2 nm, very close to the measured coating thickness (1.7 nm). The image on the right in FIG. 3B displays a TEM image of She nanopore following a 30-second exposure to the e-beam under imaging conditions (e-beam intensity: ~$10^3$ e/$nm^2$s). The surface graininess disappears yielding a surface highly resembling the uncoated membrane in FIG. 3A.

While the ex situ coating procedure is highly reliable for nanopores larger than ~10 nm, smaller pores tend to clog, in part due to accumulation of silane molecules inside the pore. To circumvent this problem, an in situ coating method, as shown in FIG. 1B was devised. In situ chemical coating is a technique for coating solid-state nanopores characterized by monitoring the chemical functionalization process as it proceeds and preventing small-dimensioned nanopores (less than approximately 10 nm in diameter) from clogging with the coating compound. In this coating mode, the nanopore is assembled in a cell containing the coating solvent and a supporting electrolyte (a salt that does not react with the surface). A voltage is applied to the nanopore, and the ionic current is measured. The coating molecule is then introduced to one of the chambers, and the current is measured in real-time as the coating proceeds. Thus, in certain applications, the in situ method is preferred over the ex situ method insofar as it prevents clogging of nanopores due to polymerization of the coating molecule in the pore and it provides information regarding the coating kinetics as the coating progresses.

In situ measurements may be used to probe the coating kinetics in real time. Coatings comprising amine terminated groups, particularly useful due to their wide range of applicability, may be applied with the in situ coating method. A second, selective layer, may be formed on amine-coated pores. The corresponding adsorption kinetics can be observed by monitoring the ion-current flowing through single nanopores. The characteristic adsorption timescale is comparable with bulk adsorption onto planar surfaces, suggesting high reactivity on the nanopore surface.

Figure 4:
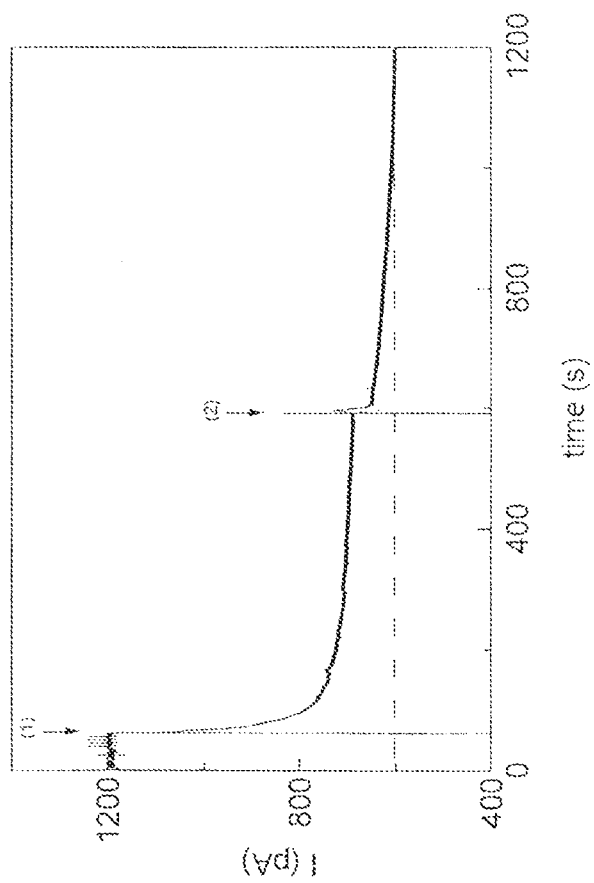
FIG. 4 illustrates a current-time trace for the in situ coating of a 5 nm nanopore using aminosilane, according to one embodiment of the invention.
Figure 6A:
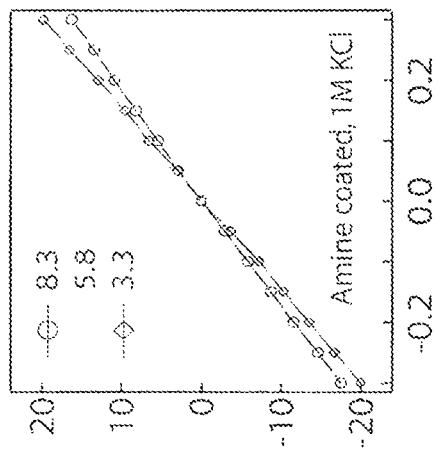
FIGS. 6A-6D illustrate I-V curves for coated and uncoated nanopores at indicated pH levels, according to various embodiments of the invention.
Figure 6B:
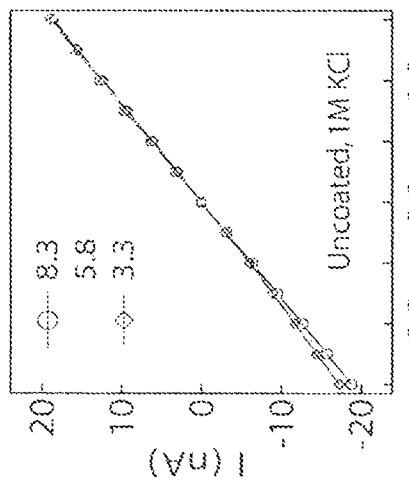
Figure 6C:
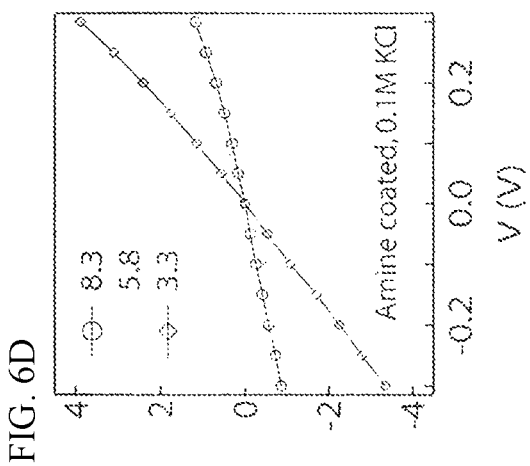
Figure 6D:
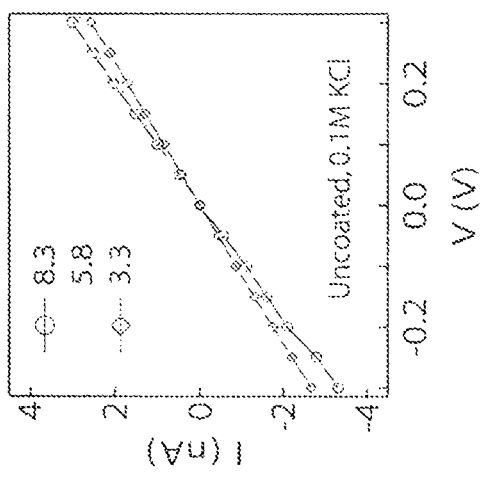

The coated nanopore, according to the example presented, is stable over days, even under treatments with voltage pulses of up to 5 V. This stability is noteworthy because silane monolayers can degrade under in vitro solution conditions. Amine-coated nanopores exhibit pH sensitive conductance. However, due to the small dimensions of the nanopores, a 4-fold difference in the conductance at physiological ionic strengths (0.1 M) may be observed. Coated nanoscale pores can thus be used to fabricate ultra small and sensitive pH sensors Chemically-modified nanopores fabricated in inorganic membranes open a wide range of possibilities for stochastic sensing. For example, amine-terminated groups can be used to immobilize protein receptors in a robust, nearly two-dimensional device. The planar geometry employed allows straightforward multiplexing using nanopore arrays. The chemically-modified nanopores may be used to gate single-molecule transport In the in situ chemical coating approach, silane is mixed with organic electrolyte in anhydrous solvent, and a voltage is applied across, the nanopore during the deposition process. The electric field induces flow of electrolyte across the nanopore, which effectively slows down the molecular adsorption kinetics. Exemplary techniques are illustrated in FIG. 4, in which the coating of a 5 nm pore with aminosilane 3 is monitored overtime. FIG. 4 illustrates a current-time trace (measured at 400 mV) for the in situ coating of a 5 nm nanopore using aminosilane 3 (supporting electrolyte: 0.5 M TBACl, solvent: anhydrous MeOH). Equal aliquots of 3 were injected at points 1 and 2. Anhydrous MeOH was used as the solvent and 0.5 M tetrabutylammonium chloride (TBACl) as the supporting electrolyte. The injection of 3 at 50 s, (arrow 1) resulted in a nearly exponential decrease in the current from 1.2 nA down to ~0.7 nA, with a characteristic time scale of 17 s. The addition of an equal aliquot of 3 at 600 s (arrow 2) caused only a minor decrease in the current, from 0.7 nA to ~0.6 nA. The first aliquot of 3 resulted in monolayer deposition on the pore surface. Based on the molecular thickness of 3 (0.7 nm, see Table 1), a single monolayer decreases the pore cross-sectional area by 42%. This value is in excellent agreement with the measured reduction in current of 42%. The minor additional decrease in the current after the second addition of 3 is attributed to dilution of the electrolyte by the uncharged silane. Similar results were obtained in repeated measurements.

FIG. 5A illustrates current-time traces (measured at 100 mV) for the addition of 2% 6 to the cis chamber of a bare 10 nm (I) and amine-coated 12 nm nanopore (II). FIG. 5B illustrates normalized change in the ion current (measured at 100 mV, 1 M KCl buffered with 10 mM phosphate to pH 5.8) of 12 nm diameter nanopores coated with aminosilane 3 upon the addition of gluteraldehyde (6) to final concentrations of 0.4% (a), 1% (b), and 2% (c) in the cis-chamber (at t=0). The bulk conductivities of the GA solutions were adjusted in order to match that of the electrolyte (161±1 mS). The inset, FIG. 5C, illustrates time constant (τ) fitting results to first-order adsorption kinetics for tire different concentrations. The solid line is a best fit to the data.

A mine-modified surfaces are versatile platforms for a wide range of applications in biotechnology. For example, glutaraldehyde (6) is a common reagent used for coupling amine-modified surfaces with proteins. Coated nanopore functionality was tested by monitoring the reaction of the amine-coated nanopores with glutaraldehyde. FIG. 5A displays an ion current trace (measured in 1M KCl aqueous solution, pH 5.8) of a 12 nm nanopore pre-coated with aminosilane 3. Upon the addition of 6 at t=0 (to a final concentration of 2%), G quickly drops by ~50% and stabilizes at a level of ~1.5 nA (II). To show that the current reduction is specifically due to reaction with the amine-coated nanopore, a current trace measured during the addition of 2% of compound 6 to an uncoated 10 nm pore (T) is displayed, which resulted in only 6% change in G. This illustrates the specificity of the glutaraldehyde reaction on amine coated pores.

The reaction kinetics inside an amine-coated nanopore also shows dependence on the bulk concentration of 6. In FIG. 5B, three ion-current traces obtained during addition of 6 at bulk concentrations of 2.0%, 1.0% and 0.4% v/v are shown. These curves were fitted to first-order adsorption kinetics, yielding a linear dependence on concentration (FIG. 5C, inset). In all cases, the steady state ion-current levels after the addition of 6 were 50±10% of the initial pore currents.

Aside from the bulk concentration of ions, surface charges may also affect ion-transport through nanoscale channels. To investigate this effect in the nanopores, the amino groups are protonated upon lowering the solution pH. Since surface ammonium $pK_a$ values are lower ($pK_a$~5-6) than in solution ($pK_a$~9), one expects to observe a strong ion conductance oil dependence around pH 5-6.

FIG. 6 shows the I-V curves of an 12 nm uncoated nanopore (A), and an amine-coated nanopore (after APTMS-coating) (B), at 1.0 M KCl, at pH 3.3, 5.8 and 8.3. FIGS. 6(C) and (D) show IV curves for similar measurements at 0.1 M. KCl for the same uncoated and coated nanopores. The coated pore conductance shows high pH sensitivity at the low ionic strength level. At 1M KCl, both coated and uncoated pores exhibit a weak pH dependence on conductance. In contrast, the coated pore displays a marked current enhancement (~4 fold), going from pH 8.3 down to pH 3.3, while the uncoated pore remains insensitive to pH even at the low ionic strength.

To explain the marked pH sensitivity of the coated pores the pore current may be written as:

$$I \approx \frac{\pi d^2}{4}\sigma_B\left(1 + 4\frac{\lambda_o}{d}\varepsilon\right), \qquad (1)$$

where $\sigma_B$ is the bulk mobilities of the KCl ions, $\lambda_D$ the Debye length (effective double-layer thickness), and $$\varepsilon = \frac{a_s\, a_o}{a_s}$$

the mobility enhancement (or reduction) near the surface. At 1M KCl, $\lambda_D$ is roughly 0.3 nm, thus $$\frac{\lambda_D}{d} \ll 1$$

and surface effects are small. On the other hand, at 0.1M KCl, $\lambda_D \sim 1$ nm, thus $$\frac{\lambda_D}{d} \sim 0.1,$$

leading to a significant pH dependence on the ion-conductance. These results are in agreement with measurements performed in track-etched PETP pores, which have native carboxylic groups on their surface.

Coating Chemically-Modified Solid-State Nanopores

The following chemicals may be used in coating the solid-state nanopores, according to certain embodiments. Toluene (Burdick & Jackson, A R) was dried by distillation from $CaH_2$ and storage over activated 4 Å molecular sieves. MeOH, $CHCl_3$, and $CH_3CN$ (anhydrous, Baker) were used as received. Glycidyloxypropyltrtimethioxysilane (1, Alfa-Aesar, 97%), methoxyethoxyundecyltrichlorosilane (2, Gelest, Inc., 95%), 3-aminopropyltrimethoxysilane (3, Acres, 95%), adipoyl chloride (4.97%, Alfa Aesar), 1,4-diaminobutane (5, Alfa Aesar, 99%), glutaraldehyde (6, 25% in water. Acros), and all other common reagents were used as received.

In other embodiments, chemical modification of solid-state nanopores entails the use of other chemicals including, for example, various silanes. These silanes include, without limitation, 3-glycidoxypropyltrialkoxysilanes with C1-6 alkoxy groups, trialkoxy(oxiranylalkyl)silanes with C2-12 alkyl groups and C1-6 alkoxy groups, 2-(1,2-epoxycyclohexyl)ethyltrialkoxysilane with C1-6 alkoxy groups, 3-butenyl trialkoxysilanes with C1-6 alkoxy groups, alkenyltrialkoxysilanes with C2-12 alkenyl groups and C1-6 alkoxy groups, tris[(1-methylethenyl)oxy]3-oxiranylalkyl silanes with C2-12 alkyl groups, [5-(3,3-dimethyloxiranyl)-3-methyl-2-pentenyl]trialkoxysilane with C1-6 alkoxy groups, (2,3-oxiranediyldi-2,1-ethanediyl)bis-triethoxysilane, trialkoxy[2-(3-methyloxiranyl)alkyl]silane with C1-6 alkoxy groups and (C2-12 alkyl groups, trimethoxy[2-[3-(17,17,17,17-trifluoroheptadecyl)oxiranyl]ethyl]silane, tributoxy[3-[3-(chloromethyl)oxiranyl]-2-methylpropyl]silane, any alkylsilane where the alkyl groups have a varying length between 3 and 30 carbons, and combinations thereof.

The nanopores are be formed in a solid-state membrane or substrate. A variety of solid-state membranes may be used including those comprising silicon nitride, silicon dioxide, silicon oxynitrides of varying compositions, as well as other metal oxides with react with silanes (e.g. aluminum oxide, titanium oxide, etc.). In certain embodiments, low-stress SiN membranes (50×50 μm$^2$, either 20 or 50 nm thick) may be used. Nanopore fabrication was carried out on the membranes using a JEOL 2010F field emission TEM operating at 200 kV, which was also used for imaging the nanopores. The nanopore fabrication process is known in the art and described at length in publications including: Kim, M. J.; Wanunu, M.; Bell, D. C.; Meller, A. *Adv. Mater.* 2006, 18, 3149-3153, herein incorporated by reference in its entirety.

The ex situ method for nanopore coating includes the following steps. Before coating, nanopore chips were first cleaned by boiling in piranha solution (1:3 $H_2O_2$:$H_2SO_4$) for 15 minutes, followed by rinsing in 18 MΩ water, filtered MeOH, and drying at 100° C. for 5 min. Coating with 1 was performed by immersion of the clean chip into 0.1% 1 in toluene for 1 h, followed by agitation in fresh toluene (8×3 ml) for 10 min, drying under $N_2$ and baking at 100° C. for 1 h. Coating with 2 was performed by immersion into a 2 mM solution of 2 in toluene for 20 min, followed by agitation in fresh toluene (8×3 ml) for 10 min, washing with MeOH, water, and drying under $N_2$. Coating with 3 was performed by immersion into a 5% solution of 3 in MeOH for 3-6 hours, followed by 10-15 min agitation in MeOH (8×3 ml), drying under $N_2$, and baking at 100° C. for 30 min. Reaction of the aminosilanized chip with 4 was performed by immersion in a 5% solution of 4 in anhydrous toluene under $N_2$ for 30 min, followed by agitation in fresh toluene 8 times and drying under $N_2$. Subsequent reaction with 5 was performed by immersion into a 1% solution of 5 in 1:1 $CHCl_3$:$CH_3CN$ for 2 h, rinsing with MeOH (8×3 ml), water, and drying under $N_2$. Other ex situ nanopore coating methods are envisioned, the above steps providing one illustration.

The coating may be characterized using various methods. In one embodiment, the different coatings were characterized on Si substrates onto which 50 nm low-stress SiN layer was deposited by LPCVD. An ES-1 (V-VASE32) Woollam spectroscopic ellipsometer was used to characterize the film thickness. AFM was performed using Veeco Instruments Multimode operating in the tapping mode. All measurements were performed using the same 10 nm tip with a cantilever frequency of 250 kHz. A SSX-100 Surface Science XPS instrument equipped with a Monochromatic Al-kα source was used for analyzing the films. A spot size of 0.6 mm was used, the takeoff angle was 45±10°, and the chamber pressure was $10^{-9}$-$10^{-10}$ torr.

Ion-conductance measurements establish a baseline against which ion-current variations may be detected. The ion-conductance of nanopores was checked by mounting the chip in a two-chamber cell such that both sides of the nanopore are separated. In order to wet the nanopore, the chip was wet on the cis side with ca. 5 μl MeOH, filled from the trans side with degassed electrolyte, and then the MeOH was gradually diluted from the cis chamber by flushing with electrolyte. Two Ag/AgCl electrodes were inserted into each chamber, and the leads were connected to an Axopatch 200B amplifier. I-V curves were then recorded at intervals of 50 mV and the conductance calculated from the slope of the curve.

For pH conductance measurements, solutions of different pH values were prepared using 10 mM phosphate buffer, and the bulk conductivities of all solutions at a given ionic strength were adjusted (using a conductivity probe) to within 0.5% by the addition of KCl.

The in situ method for nanopore coating includes the following steps. Silanization of nanopores with 3 was performed by filling both chambers of a clean, 5 nm nanopore, with 0.5M TBACl in anhydrous MeOH. The current was recorded at 400 mV with 100 Hz sampling rate. 5 μl aliquots of 3 were added to ~150 μl in the cis chamber. In situ reaction of amino-terminated nanopores with glutaraldehyde 6 was performed by mounting nanopores coated with 3 in a nanopore setup and filling the chambers with 1 M KCl, buffered with 10 mM phosphate to pH 5.8. A flow cell was used to introduce different concentrations of 6 to the cis chamber. To avoid conductance changes due to electrolyte dilution, the conductivity of solutions containing 6 were adjusted with KCl to match that of the electrolyte in the chambers.

Applications

The coated nanopores may be used in the following applications: (1) tuning the analyte-pore interactions by chemical modification of pore surfaces; (2) articulating solid-state nanopore sensors with proteins; and (3) localized environmental sensing.

(1) Tuning the Analyte-Pore Interactions by Chemical-Modification of Pore Surfaces Nanopores are an emerging class of single-molecule sensors capable of probing the properties of nucleic acids and proteins with high-throughput and resolution Nanopores are extremely sensitive single molecule sensors, which have been recently used for the detection of biopolymers such as DNA and RNA. One of the most promising applications for nanopores is ultra-fast DNA sequencing. An outstanding issue in the implementation of nanopore sequencing is the high speed at which the biopolymers translocate through the pore. In order to distinguish between the four different nucleotides in the DNA, a sufficient integration time should be realized in the readout process. Current results show that the translocation time of each single nucleotide is two to three orders of magnitude faster than the desired speed. Although efforts have been made to reduce the translocation speed, e.g., by increasing the fluid viscosity, only a small decrease of the speed was observed, coupled to attenuation of the ion current signal used for nucleotide probing. Current decreases with increases in viscosity, resulting in a decreasing signal-to-noise ratio and ion current signal degradation.

FIG. 7A illustrates the translocation of biopolymers, such as DNA molecules, through uncoated (bare) silicon nitride nanopores 700 is too fast, and on occasion, results in irreversible sticking to the nanopore 700. FIG. 7B illustrates how the coating of the nanopores 700 with uniform layer of short polymers (coating 720) can be used to avoid sticking and to reduce translocation speed of the biopolymer (710).

The inventors have indicated that the main factors affecting DNA 710 translocation speed in nanopores 700 are associated with the pore-biopolymer interactions, at the pore walls. Thus, it may be preferable to target these interactions, rather than changing global properties, such as the solution viscosity. The methods described in this invention set the stage for specific, interaction-based chemical modification that can be used to slow down DNA 710 translocation. In particular, grafting short organic polymers 720 inside the nanopore 700 (see FIGS. 7A and 7B) can hinder the DNA electrophoretic mobility by interactions with DNA 710 at the nanopore volume. The disclosed methods can be tested with a number of different polymer chains and end-groups to target specific biopolymer interactions. For example, cationic (+) groups, such as polyamines, may slow down DNA translocation by electrostatic attraction to the anionic (−) DNA molecule. Surface-bound ion chelators (e.g., $Zr^{4+}$, $Ce^{4+}$) may also retard DNA tranlocation by weak coordination to the phosphate backbone of the DNA molecule.

In nanopore experiments such as those depicted with reference to FIGS. 7A and 7B, a voltage is applied across a thin insulating membrane containing a nanoscale pore 700, and the ion current of an electrolyte flowing through the pore is measured. Upon introduction of charged biopolymers to the solution, the local electrical field drives individual molecules through the nanopore 700. Passage of biopolymers 710 through the pore causes fluctuations in the measured ion current that directly correspond to their local cross-section. While other single-molecule techniques (e.g., atomic force microscopy) rely on a movable sensor to detect the properties of surface-immobilized biomolecules 710, the nanopore is spatially fixed, with the molecules being driven to the nanopore sensor 700. This allows a very large number of single biopolymers to be probed without chemical modification (conserving structure/function). This also eliminates the need for surface immobilization, thereby providing higher throughput. These attractive features have set the stage for the development of novel nanopore-based applications, such as detection of genetic variability, probing DNA-protein interactions, and low-cost, high-throughput DNA sequencing.

Central to all such nanopore methods is the objective of controlling the translocation process at a level that allows spatial information to be resolved at the nanometer scale, within the finite time resolution imposed by instrument bandwidth and noise. To achieve this goal, developing a fundamental understanding of the factors governing the DNA translocation dynamics, and its relationship with the magnitude and fluctuations in the blocked current signal, is desirable. To date, most DNA translocation studies have been performed using the toxin α-hemolysin (α-HL), which can only admit single-stranded DNA. (ssDNA) and RNA (but not double-stranded nucleic acids). Typical translocation velocities for ssDNA through the α-HL channel are $v_\tau \sim 0.2$ mm/s (measured at 120 mV and RT), corresponding to translocation times of $\tau_{96}$ (N)=$1/Nv_\tau \approx 2$ μs/base (N=number of nucleotides. 1 is the DNA contour length), approaching feasible temporal resolution for single-base detection. However, biotechnological nanopore applications require size tunability and membrane robustness, not available with phospholipid-embedded protein channels.

Recent progress in the fabrication of nanoscale materials has enabled the reproducible formation of artificial, well-defined nanopores its thin, solid-state membranes. Most DNA translocation studies have focused on relatively large pores (8-20 nm), for which the translocation dynamics were markedly faster ($v_\gamma \sim 10$ mm/s or 30 ns/bp). In addition to the fast dynamics, the use of large nanopores necessitated performing measurements at smaller temporal bandwidths than with α-HL experiments (10 kHz vs. 100 kHz, respectively). This results in degradation of the ion current signal, which compromises the spatial resolution of the analyzed biopolymer. Slowing down biopolymer translocation is therefore a key goal for improving the analytical capabilities of nanopores. The present techniques for providing chemical functionalization of nanopore surfaces may be used to slow biopolymer translocation, and enable this sensing applications.

Presented in Example #1, below, is a systematic investigation of the voltage-driven translocation dynamics of double-stranded DNA (dsDNA) through solid-state nanopores as a function of DNA length, temperature, and pore size, recorded at comparable bandwidths to measurements with α-HL. Results show complex dynamics, characterized by two distinct regimes where different length scaling laws prevail. Temperature dependence studies indicate the negligible role of viscous drag, pointing to the significance of DNA/surface interactions. Finally control over the nanopore size not only affects the translocation probability, but in turn has a dramatic impact on the dynamics. This holds significant implications for nanopore design, allowing the dynamics to be fine-tuned by sub-nm control over pore size. Experimental evidence indicates that DNA-surface interactions both inside and outside the nanopore govern the translocation dynamics. As a consequence, the inventors observed that for 4 nm pores that dsDNA velocities as low as 10 μs/bp can be achieved with high throughput. Such speeds are commensurate with instrumentation bandwidths, thus allowing for the first time an individual basepair to be sampled. Thus the interaction-based approach for slowing DNA favorably compares with natural α-HL channel, representing a crucial resolution improvement for future solid-state nanopore applications.

(2) Articulating Solid-State Nanopore Sensors with Proteins

Protein molecules are nature's laborers, carrying out a variety of precise tasks, such as molecular recognition, chemical catalysis, and molecular transport. By articulating the solid-state nanopores with individual protein molecules, these functions can be probed with unprecedented efficiency and sensitivity. Molecular recognition can be studied by immobilizing a single protein molecule in the nanopore, and then observing ion current blockades during binding of analytes. Enzyme catalysis can be studied at the single-molecule level by optical probing of enzymes immobilized inside nanopores, while using ion-current measurements for additional control over activity and analyte concentration. Molecular transport through protein channels can be engineered by immobilizing a single protein channel inside a nanopore. Since the immobilized protein molecule is immobilized at the junction connecting the two membrane sides, it can be subjected to chemical gradients, or conversely it can pump molecules from side to side to create chemical differences (see FIG. 7C-D). According to this invention, three classes of programmable, nanopore-based single-molecule sensors are presented:

FIG. 7C illustrates how enzymes or other proteins are specifically immobilized inside nanopores by coating the pores with organic monolayers 730 that specifically bind particular groups on the protein, immobilization of the protein 740 in the nanopore 700 opens up the possibility of applying chemical gradients on the enzyme, or to use the protein for the generation of chemical gradients, represented by the two-color background in the figure.

A. Recognition: Protein molecules having specific recognition elements, i.e., antibody epitopes, can be bound to the interior of the nanopore by chemical grafting to immobilized chemical groups on the nanopores. Such recognition devices will be sensitive to various agents, being able to detect other proteins, viruses, and other pathogens. The detection is made possible by monitoring the ion-current of the nanopore. During the addition of various agents, the current will be blocked upon specific binding to the recognition element in the nanopore. The well-established specificity of the recognition, coupled to single-molecule sensitivity afforded by the nanopores, enables the fabrication of a variety of ultra-sensitive devices.

In one example, antibodies for any one of a variety of important pathogens (e.g., anthrax, *E. coli, salmonella*) can be bound to the surface of the nanopore using coupling chemistry, e.g., using amine-groups on the antibody and carboxylic groups on the surface. The nanopore is then exposed to a salted sample solution, while applying a voltage across the nanopore. Entry of a single pathogen into the nanopore volume would result in a reduction in the ion current, indicating a positive identification. The existing variety of antibodies and other specific recognition elements enable an enormous spectrum of detection schemes.

B. Catalysis: Enzymatic activity can also be probed on the single-molecule level. This can be achieved by chemically grafting a single enzyme (protein) to the nanopore cavity. Using glutaraldehyde-functionalized nanopores, it is possible to fix single protein molecules inside nanopores by reaction of surface aldehydes with amine groups on the surface of the protein molecule. This reaction is well-known on planar surfaces, although it has never been demonstrated inside a nanopore surface. Enzymes catalyze the chemical conversion of specific molecules (substrates). Using a fluorophore-labeled substrate, the turnover (conversion rate) for a single enzyme molecule can be probed in real time using optical microscopy.

In one example, the proton pump ATP synthase is a reversible coupling device that can convert the electrochemical potential in proton gradient into chemical bond energy, or vice versa, ATP synthase. In bacteria the ATP synthase pumps protons ($H^+$ atoms) through the mitochondrial inner membrane, against a chemical potential, by hydrolyzing ATP molecules. Conversely, it can generate ATP from ADP by proton flow. These processes are done with great efficiency. This enzyme is composed of a static part known as the "stator" and a rotation portion known as the rotor. During catalysis the rotor moves and can generate torque. In this respect ATP synthase is also a mechanical motor. Harnessing biological pumps and motors may be realized if the enzymes are immobilized inside a nanopore made in structurally rigid membrane. This has three advantages over the incorporation of the enzyme in phospholipids bilayers: a) Phospholipid bilayers are fluid, thus the enzymes can diffuse in the bilayer complicating the probing, b) Solid-state membranes are more durable and robust mechanically and chemically, c) By fabricating high-density arrays of pores, one may construct dense "factories" of enzymes, which are capable of producing energy in tire form of a proton gradient.

Nanopore immobilization enables the enzyme activity, by applying voltage across the nanopore, and controlling the transport rate of different cofactors, which are essential for enzyme activity. The nanopore tool therefore affords single-enzyme localization and further control over activity.

C. Transport: Trans-membrane protein channels form robust channels across lipid bilayers, designed for selective transport of ions and molecules. Self-assembly of protein molecules to form channels is spontaneous, yielding a highly-reproducible shape down to the atomic level. Membrane-embedded channels (e.g., α-hemolysin and others) have been used to study transport of biopolymers and small molecules, emerging as highly sensitive single-molecule detectors. Despite this, the limited stability of lipid bilayers restricts the commercialization of such devices. By using solid state nanopores, in place of nanopores formed in lipid bilayers, these stability problems may be overcome. Solid state nanopores have a high degree of stability and provide a robust sensing mechanism with commercial promise. Chemically-modified nanopores containing hydrophobic moieties (e.g., alkanes) can mimic a lipid bilayer environment, enabling the spontaneous insertion of protein channels into the modified nanopores. The resulting solid-state/biological channel combination can enable long-life single-molecule sensors.

FIG. 7D illustrates immobilization of a protein channel 750 inside a nanopore 700 fabricated in a solid-state membrane. As above, nanopore 700 may be coated with organic monolayers 730 for selective binding. The robust, semi-synthetic device provides new opportunities utilizing engineered protein channels as sensors, exhibiting solid-state rigidity and durability while allowing biochemical versatility.

(3) Localized Environmental Sensing

Sensing of microscopic environments can provide a wealth, of information on processes occurring in dynamic systems, such as living cells. Probing these processes can be accomplished by probing the local environment around them. For a living cell several micrometers in length, localized sensing with spatial resolution of 10-100 nm can reveal unprecedented information on cell function. Sensing of a variety of environmental factors on these scales is a challenge which can be overcome using chemically-modified nanopores. Localized environmental sensing can be conducted with either a single nanopore or a two-dimensional array of nanopores.

Arrays of nanopores can be fabricated on a thin single solid-state insulating membrane with each nanopore separated from an adjacent nanopore on the membrane by a selected distance. Arrays of chemically-modified nanopores can be rapidly fabricated on identical silicon nitride membranes (e.g. having a thickness between approximately 5 nanometers and approximately 100 nanometers). Since the chemical modification step is performed under conditions which expose the whole membrane, the chemical modification parameters are the same for a nanopore array as they are for a single nanopore. After chemical modification of the nanopore array, various environmentally-sensitive reagents can be introduced to each nanopore, and each nanopore would behave as a localized reporter of the environment. The coated nanopore technology enables sensing of a variety of ions in solution/in contact with the nanopore surface. The two examples below are illustrative.

A. Localized pH sensing: Sensing pH is one instance of many environmental sensing applications envisioned. Using a two-dimensional array of chemically-modified nanopores, localized pH sensing can be accomplished. The nanopores are functionalized with a pH-responsive chemical group, i.e., a fluorophore, and the device is placed above a fluorescent microscope. At any particular solution pH, the array displays a constant intensity. However, upon a local change in pH, intensity variations can be seen.

For example, by equipping a nanopore with various fluorescent probes refined sensing of a variety of ions and small molecules is possible. According to certain embodiments, calcium and phosphate can be detected by various sensor systems well-known in the art. In each environmental sensing application, optical detection approaches entail probing the fluorescence intensity of a fluorophore embedded in a nanopore as a function of time. When the nanopore is subjected to the analyte ion, the fluorescence intensity changes as a result of changes to the conformation and/or structure of the fluorphore. In this example, the binding of four $Ca^{2+}$ ions to a calmodulin-M13 moiety in a Calcium Sensor induces a conformational change to the protein-based sensor. This change brings the cyan fluorescent protein (CFP) and yellow fluorescent protein (YFP) domains closer, allowing fluorescence resonance energy transfer (FRET) to occur (resulting in modulation of the tight intensity at the pore).

B. Spatial concentration sensing using arrays: Spatial variations in analyte concentration may be sensed using nanopore arrays. Using arrays similar to those disclosed above, it is possible to coat nanopores with fluorophores which are sensitive to ions and molecules. For example, phosphate ions can be visualized by immobilizing malachite green onto the nanopores, ATP can be sensed by immobilizing luciferase in the presence of luciferin, etc. In this application, the gradient of the molecules (or ions) to be detected is probed by sensing the fluorescence intensity spatial distribution. The nanopore array serves two functions: 1) to spatially immobilize the probe molecules in given locations and 2) to support objects such as live cells on solid surfaces.

EXAMPLES

Example #1: Unfolded DNA Translocation Governed by Interactions with Solid State Nanopores Experimentation has verified voltage-driven translocation dynamics of individual DNA molecules through solid-state nanopores. Nanopores with diameters slightly larger than the DNA cross-section (approximately 2.2 nm) may be used to reduce translocation times. In certain embodiments, the translocation times of DNA molecules are slowed by approximately one to two orders of magnitude. Experimental evidence reveals that both temperature and the nanopore size strongly affect the dynamics. While not wishing to be bound by theory, the inventors believe this effect implies that interactions between DNA and the membrane are the rate-limiting step for translocation, as opposed to viscous drag. For DNA longer than ~10 Kuhn lengths, a crossover in the scaling of the translocation dynamics to a slow regime is observed. Furthermore, experimental results suggest the DNA current blockage is length dependent above the transition point, supporting a model involving DNA/membrane interactions outside the nanopore. The evidence of slower dynamics corresponds to ~10 µs/bp, measurable using state of the art instrumental bandwidth (100 KHz).

FIG. 8 shows a solid-state nanopore device for single-molecule analysis. FIG. 8A illustrates a schematic view of a solid state nanopore device for probing DNA translocation dynamics, according to one embodiment of the invention. The apparatus for solid-state nanopore experimentation is shown. DNA molecules are driven through the nanopore by an applied voltage, while the ion current of an electrolyte is measured. Dynamic Voltage Control is used to automatically unclog the nanopores when a molecule remains in the pore for a prolonged time. According to the present embodiment, nanopores are drilled with sub-nm resolution, and ion conductance measurements are used to better estimate the actual nanopore size, d, as previously described in *Rapid fabrication of uniformly sized nanopores and nanopore arrays for parallel DNA analysis* (Kim M J. Wanunu M, Bell D C, Meller A. (2006) *Adv. Mater.* 18:3149-3153).

FIG. 8B shows a plot of a typical ion current trace for a 4 nm solid state nanopore before and after introducing DNA sample to the cis chamber (indicated by arrow), according to one embodiment of the invention. The transient current blockade events correspond to single-molecule translocation of DNA. The inset displays a magnified set of translocation events of 400 bp DNA, with the described relevant parameters (baseline data between events has been removed in order to increase the displayed time resolution). Upon addition of dsDNA into the cis chamber (arrow "DNA" FIG. 8B), a distinct stochastic current blockade events may be observed. The rate of the events scales with DNA concentration. To confirm that the observed current blockade events correspond to DNA translocation experimentation showed that a 400 bp fragment placed in the cis chamber could be found in the trans chamber following ~6,000 current blockade events. A trace of current blockade events with a greatly expanded time axis is shown in the inset to FIG. 8B. Several parameters are defined here: the event duration (or dwell-time), $t_D$, the mean blocked pore current, $\langle i_b \rangle$, and the fractional current, $I_D = \langle i_b \rangle / \langle i_0 \rangle$ in normalized units ($I_B = 0$ corresponds to a fully blocked pore).

DNA translocation dynamics in interactions with solid state nanopores may be experimentally evaluated in regard to (1) the effect of pore size on DNA translocation probability, and (2) the dependence of translocation dynamics on DNA length, temperature, and nanopore size. The findings in regard to each aspect are described at length below.

(1) Effect of Pore Size on DNA Translocation Probability.

Figure 9:
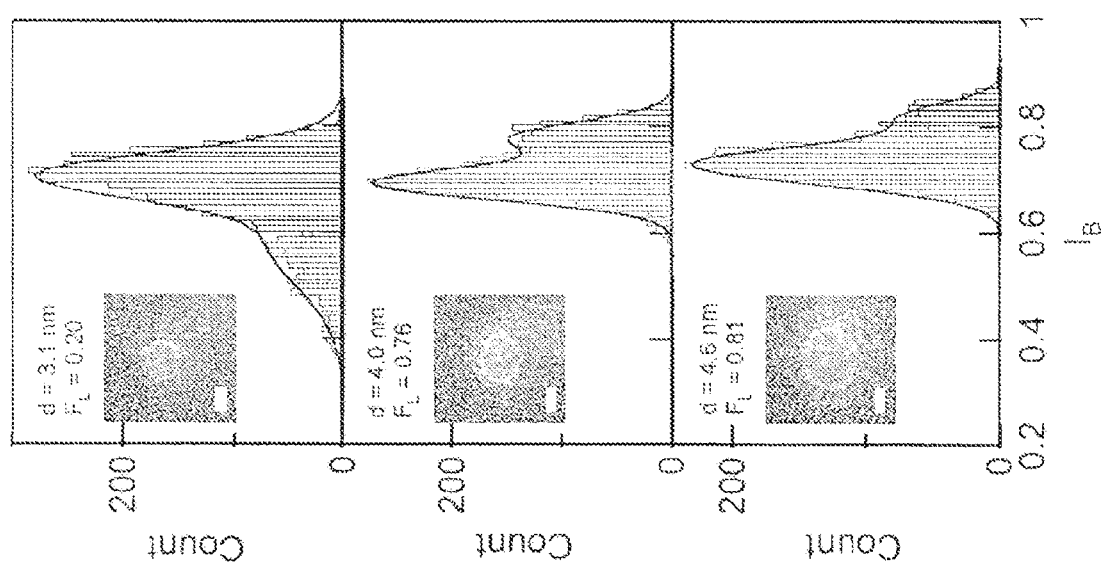
FIG. 9 illustrates histograms of blocked current levels, and insets showing TEM images of nanopores, according to various embodiments of the invention.

The effect of nanopore size on DNA translocation probability was experimentally examined. FIG. 9 illustrates histograms of blocked current levels, and insets showing TEM images of nanopores, according to various embodiments of the invention. Specifically, the histograms show the blocked current levels, $I_B$, measured for >3,000 translocation events of 400 bp DNA at 300 mV using three different nanopore diameters, 3.1 nm, 4.0 nm and 4.6 nm (a-c, respectively). The insets are TEM images of nanopores with corresponding sizes (scale bars=2 nm). The current histograms clearly showed two normal populations, as seen by a fit to a sum of two Gaussian functions (black curves). The high current event ($I_{BH}$, dark grey) and the low current event ($I_{BL}$, light grey) populations, as well as the low-current fraction $F_L$, are defined in the text.

The histograms clearly show that all events fall into one of two populations (dark and light grey), which are well-represented as a sum of two normal distributions (black traces). The cutoff current, $I_{cut}$, is established to be the local minimum between the two peaks denoted as $I_{BH}$ (high current peak, dark grey) and $I_{BL}$ (low current peak, light grey). The fraction of the low current events is approximated by: $F_L = n_L/(n_L + n_H)$, where $$n_L = \int_0^{I_{on}} H(I)dI \text{ and } n_H = \int_{I_{off}}^1 H(I)dI,$$

and H(I) is the measured histogram of events with normalized blocked current I, and dI is the bin size $F_L$ systematically increases from 0.20 to 0.81 as the pore diameter increases from 3.1 to 4.6 nm. In addition, the values of both $I_{BH}$ and $I_m$ increase with the nanopore size.

Figure 10:
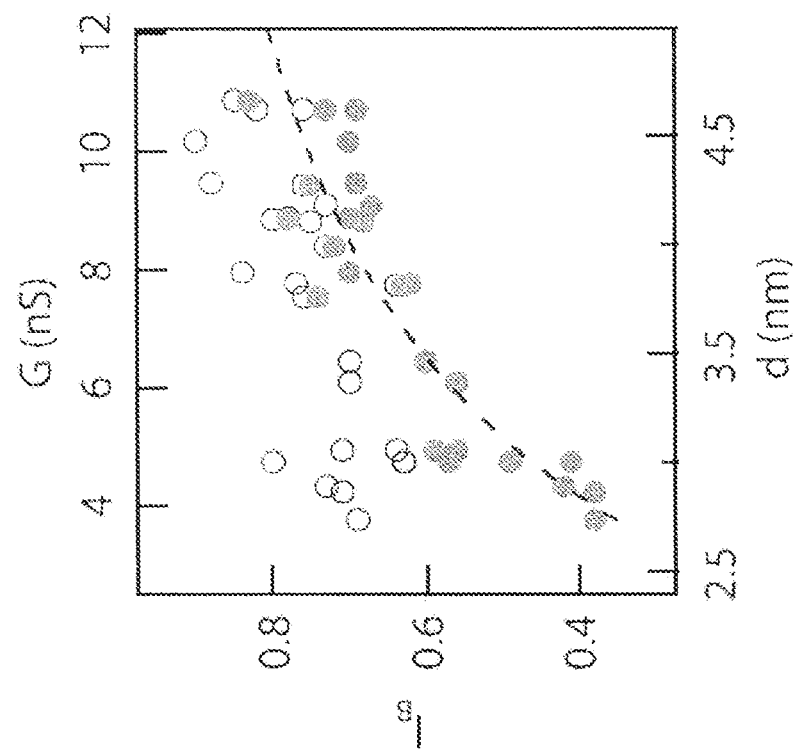
FIG. 10 illustrates a plot of experimental current levels and theoretical current levels for a series of nanopores with different diameters, according to one embodiment of the invention.

Further quantitative representation is provided in FIG. 10. FIG. 10 illustrates a plot of experimental current levels and theoretical current levels for a series of nanopores with different diameters, according to one embodiment of the invention. Specifically, it shows $I_{BL}$ (light) and $I_{BH}$ (dark) values for a series of 25 nanopores with different diameters in the range 2.7-4.6 nm. In FIG. 10, $I_{BH}$ and $I_{BL}$ values are plotted as a function of d for 25 different nanopores under identical experimental conditions (400 bp DNA, 300 mV, 21° C.). Although pores with similar G values exhibit a variance in average $I_H$ values, attributed to pore-to-pore variability, the values of $I_{BH}$ and $I_{BL}$ follow a trend, regularly increasing with d. The dashed line is the theoretical $I_B$ curve based on Eq. 1 with α=2.2 nm, showing excellent agreement with $I_{BL}$, while clearly deviating from $I_{BH}$. Notably, $I_m$ shows greater pore size dependence than $I_{BH}$, especially for pores with d<3.1 nm, where $I_{BL}$ begins to decrease sharply. The fractional blockage ($I_B$) for full dsDNA threading may be approximated by a purely geometric expression (dashed line in FIG. 10):

$$I_B^*(d) = 1 - \frac{a^2}{d^2} \quad \text{(Eq. 1)}$$

where a=2.2 nm is the hydrodynamic cross-section of B-form dsDNA. Eq. 1 does not involve any scaling factors or fitting parameters, allowing for direct theoretical $I^*_B$ values compared with experimental $I_B$ values. Referring back to FIG. 10, this estimation (dashed line) coincides well with experimental $I_{BL}$ values, while clearly deviating from the trend of $I_{BH}$ values. The agreement for $I_{BL}$ values, as well as the dramatic change in relative populations with pore size, suggest that events in population $I_{BH}$ may correspond to unsuccessful threading attempts, while events in population $I_{BL}$ are translocations.

Further experimentation has indicated a correlation between the dwell-time dynamics and $I_B$ values. FIG. 11 A-C illustrate plots of typical dwell-time distributions for different DNA lengths, according to various embodiments of the invention. Specifically, FIG. 11A-C present dwell-time distributions for N=a) 400 bp, b) 2,000 bp and c) 10,000 bp, respectively. For each DNA length, >3,000 events have been collected and sorted according to their $I_B$ population (see FIG. 9), where dark and light grey dwell-time bins correspond to events in $I_{BH}$ and $I_{BL}$, respectively. The dwell-time histograms show several distinct characteristics. First, for all DNA lengths, events in $I_{BH}$ (dark) have extremely short dwell-times (~50 Ξs). Second, events in $I_{BL}$ (light) display a more complex dwell-time distribution which are highly sensitive to the DNA length, with $t_d$ values extending to several ms. Double-exponential fits (black curves) for each distribution in $I_{BL}$ yields two timescales, denoted as $t_1$ and $t_2$. Finally, the $t_d$ values for events in $I_{BL}$ (light) clearly exhibit a strong DNA length dependence, while events in $I_{BH}$ (red) maintain a very weak length dependence.

Experimental evidence thus reveals: 1) Events in $I_{BH}$ populations display extremely short, weakly length-dependent timescales, 2) there is a striking agreement between $I^*_B$ and measured $I_{BL}$ values, 3) events in $I_{BL}$ exhibit longer dwell-times, in addition to being length dependent. While not wishing to be bound by theory, the inventors believe these combined findings support the hypothesis that events in $I_{BH}$ correspond to DNA collisions involving unsuccessful threading, while events in $I_{BL}$ are translocations. This is in accordance with findings that for the protein pore α-HL, short (~10 μs) and shallow events are attributed to random collisions with the pore, while the longer events are attributed to full translocations. In accordance with the histograms in FIG. 9, the increasing proportion of events in with nanopore size reflects a significant increase in the translocation probability $I_{BL}$ and a corresponding decrease in non-translocating collisions.

In further reference to the dwell-time distributions of events in $I_{BL}$ population (FIGS. 11A-C), distribution at dwell times longer than the peak value may be approximated using decaying exponential functions. Although mono-exponential functions were found to inadequately describe the data, >99% of the dwell-time events in the distributions could be modeled as a sum of two exponential functions, yielding two timescales, $t_1$ and $t_2$, with two corresponding amplitudes, $a_1$ and $a_2$ (see black curves in FIG. 11A-C). Based on these fits, characteristic timescales for three different DNA lengths are indicated, clearly showing strong length dependence on both $t_1$ and $t_2$. The coexistence of two distinct, length-dependent timescales points to two translocation mechanisms, as discussed in the next section.

Figures 12A, 12B:
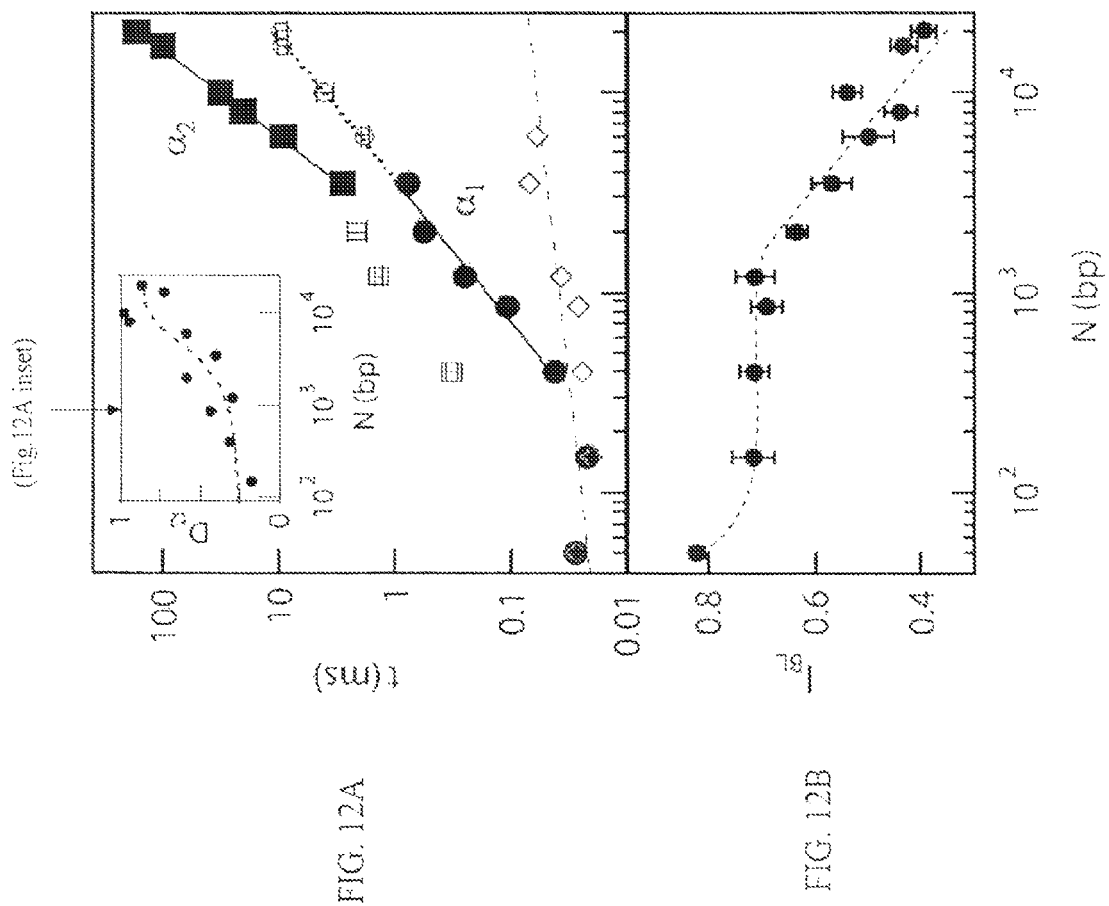
FIG. 12 A-B illustrate a log-log plot and a semi-log plot of DNA translocation dynamics as a function of DNA length, according to one embodiment of the invention.

(2) Dependence of Translocation Dynamics on DNA Length, Temperature and Nanopore Size The dependence of translocation dynamics on DNA length, environmental temperature and nanopore size was experimentally examined. FIGS. 12A-B illustrate log-log and semi-log plots of DNA translocation dynamics as a function of DNA length, according to one embodiment of the invention. In FIG. 12A, translocation timescales $t_1$ and $t_2$, as well as the collision time-scale $t_0$, as a function of the DNA length N are displayed. FIG. 12A provides a log-log plot of DNA translocation dynamics as a function of DNA length measured at 21° C., 300 mV using a 4 nm pore. Three timescales are identified: $t_0$ (open diamonds) attributed to collisions with the pore, $t_1$ (circles) attributed to short translocations events, and $t_2$ (squares) attributed to long translocation events. As previously noted, $t_0$ exhibits an extremely weak length dependence, as shown by the dashed line. In contrast, the translocation timescales $t_1$ and $t_2$ exhibit a strong dependence on N. Specifically, a crossover between, two power laws was observed, where each power law was dominant in a different size regime: For N<3,500 bp, $t_1 \sim N^{a_1}$, where $a_1$=1.40±0.05. whereas for N>3,500, a steeper power law emerges, $t_2 \sim N^{a_2}$, where $a_2$=2.28±0.05. Quantitatively, this transition may be represented as a shift in the relative fraction of long to short events, defined by $D_a = a_2 t_2/(a_1 t_1 + a_2 t_2)$.

The inset of FIG. 12A shows a transition of the fraction of total translocation events ($D_{r2}$). The FIG. 12A inset points to a gradual transition from a $t_1$-dominated regime to a $t_2$-dominated regime at N≈3,500 bp, where both populations are nearly equal. For each DNA length, solid markers are used to designate the dominant timescale. For very short DNA molecules (n≤150 bp), there is a significant overlap between the values of $t_1$ and $t_0$, practically setting a cutoff for the fastest resolvable translocation (~30 μs).

FIG. 12B shows a semi-log plot of the dependence of $I_{BL}$ on N, displaying the transition from N-independent to N-dependent regimes at N≈3,500 bp. The line is a visual aid demonstrating an approximate trend. FIG. 12B displays the dependence of $I_{BL}$ on the DNA length. If one relates $I_{BL}$ solely to the geometric blockage imposed by the DNA, one would expect that for biopolymers longer than the pore length (~80 bp), $I_m$ will be independent of N. This is supported by the developed data: For N=50 bp), $I_{BL}$=0.8, while for 150≤N≤2,000 bp the inventors found that $I_{BL}$=0.65±0.05. However, for molecules longer than 2,000 bp, the inventors found a regular decrease in $I_{BL}$ with increasing N was observed. In other words, a greater fraction of ions is displaced from the pore and its vicinity during translocation of long DNA molecules. This occurs near the transition from $t_1$- to $t_2$-dominated regimes, implying a relationship between $I_{BL}$ and the dwell times.

Figure 13:
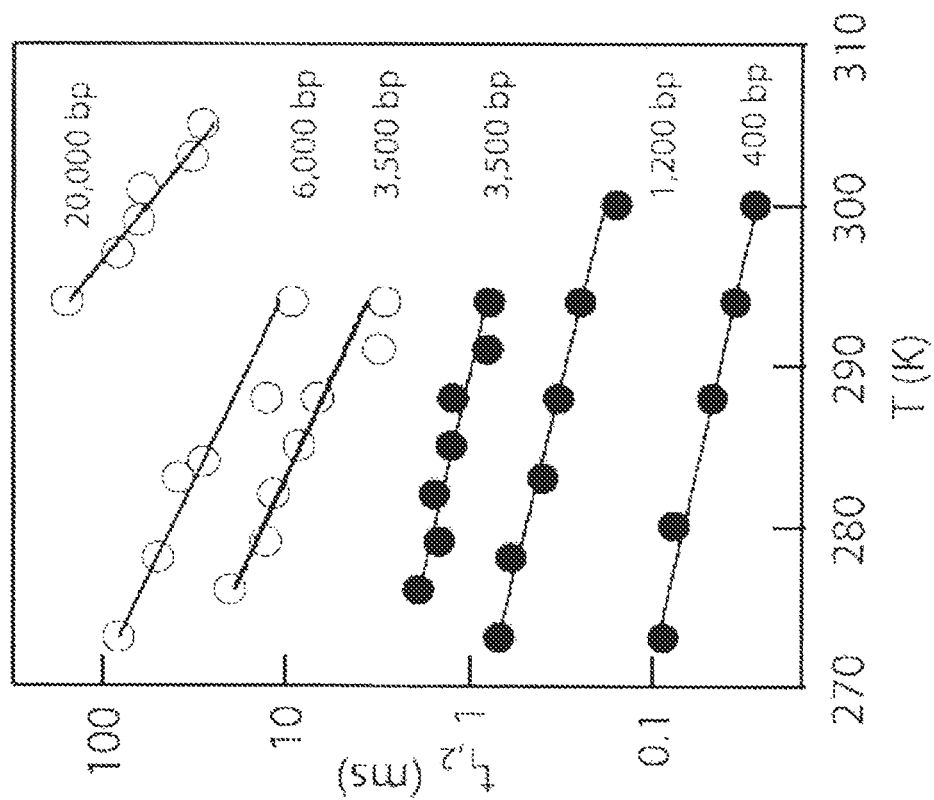
FIG. 13 illustrates a semi-log plot of the temperature dependence of the translocation times of various DNA lengths, according to one embodiment of the invention.

Furthermore, the roles of temperature (T) and the nanopore diameter (d) on the translocation dynamics have been experimentally evaluated, FIG. 13 illustrates a semi-log plot of the temperature dependence of the translocation times of various DNA lengths, according to one embodiment of the invention. FIG. 13 presents values of the most dominant timescale as a function of T for 400<N<20,000, where $t_1$ and $t_2$ values are represented with solid and open markers, respectively. The semi-log plot shows the temperature dependence of the translocation times $t_1$ (solid circles) and $t_2$ (open circles) for a number of DNA lengths.

In all such cases, the $t_1$ can be well approximated using exponential functions, $t_1$ and $t_2$ exhibit exponential dependence on T ($t \sim e^{-T/T'}$, where T' is the characteristic slope). While $t_1$ values follow a single exponential slope (T'=21.7±1.3 K), $t_2$ values exhibit considerably lower T' values, ranging from 10.5±1.0 K for 3,500 bp to 5.0±1.0 K for 20,000 bp. If the translocation times are dominated by hydrodynamic drag (either inside or outside the pore), one can expect the dynamics to be governed by the fluid viscosity, which is well-approximated by an exponential function $\eta(T) \sim e^{-T/T_a}$ in this temperature range. However, $\eta(T)$ follows a temperature slope of $T_\eta$≈39.3±0.8 K, much weaker than the temperature dependence observed for the present translocation dynamics. For instance, if translocation were governed by pure viscous drag, a 39 K temperature decrease would result in a modest increase of the translocation times (a factor of e). In contrast, the same temperature drop will increase translocation times by roughly $e^2$ for $t_1$, and >$e^4$ for $t_2$. This finding indicates that viscous drag alone cannot account for the translocation dynamics.

While not wishing to be bound by theory, the inventors believe that the strong exponential temperature dependence of the translocation dynamics, as well as the transition from $t_1$ to $t_2$ at N≈3,500 bp, suggest that interactions play a dominant role in this process. Specifically, this observed transition is likely to result front interactions of DIN A with the membrane surface, in addition to interactions inside the pore. In order to probe the relative contribution of these two effects, the inventors examined the translocation dynamics as a function of nanopore size, using a relatively stiff DNA molecule for this study in order to probe interactions inside the pore while minimizing interactions with the outer membrane surface (400 bp, or ≈1.3 b, where b is the Kuhn length).

Figure 14:
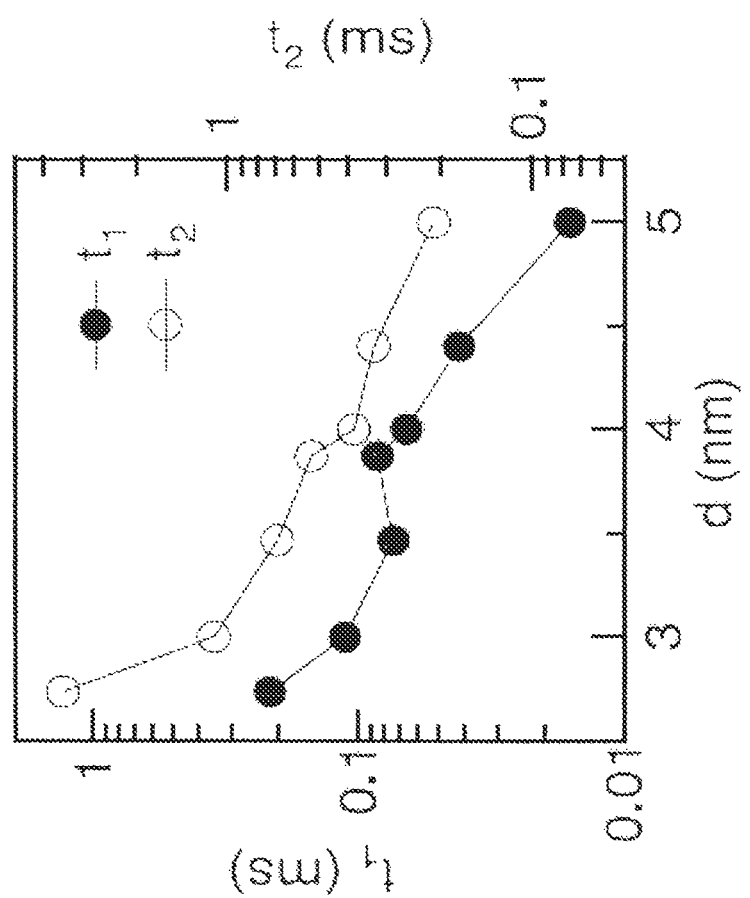
FIG. 14 illustrates a semi-log plot of DNA translocation timescales, according to one embodiment of the invention.

FIG. 14 displays semi-log plots of $t_1$ and $t_2$ as a function of d. The figure displays the semi log plots of $t_1$ (solid circles) and $t_2$ (open circles) for 400 bp DNA as a function of the nanopore diameter in the range 2.7-5 nm. Experimental results show that decreasing the nanopore size by ~2 nm resulted in an order of magnitude increase of both $t_1$ and $t_2$. As with the aforementioned temperature dependence studies, these observations are believed to rule out Stokes drag as the dominant factor governing the translocation dynamics.

Figures 15A, 15B, 15C:
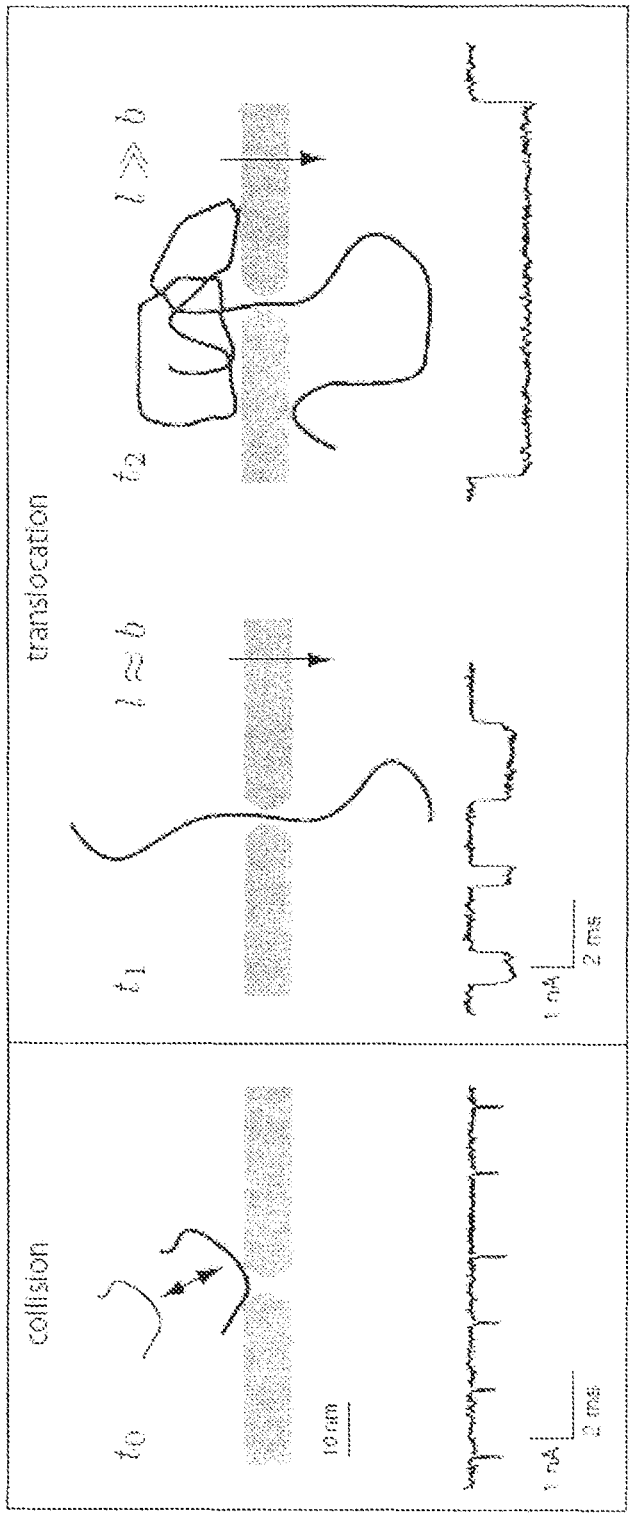
FIG. 15 A-C illustrate schematic representations of proposed mechanisms, according to various embodiments of the invention.

FIGS. 15 A-C illustrate schematic representations of proposed mechanisms, according to various embodiments of the invention. Three timescales and typical corresponding traces are shown. The translocation dynamics will depend upon the configuration of the biopolymers at the initial moment of translocation, leading to a mixture of short and long events in the translocation dwell time distributions, which correspond to loosely coiled and highly entangled DNA molecules. FIG. 15A illustrates a schematic representation of a molecular collision at time $t_0$. FIG. 15B illustrates; a schematic representation of DNA translocation for a short molecule at time $t_1$ with 1≈b, where b is the Kuhn length. FIG. 15C illustrates a schematic representation of DNA translocation for a long molecule at time $t_2$ with 1>>b, where b is the Kuhn length.

(3) Materials and Methods

Linear, dsDNA fragments in the length range 50<N<20, 000 bp were used in these experiments. The 400 bp DNA fragment was prepared by polymerase chain reaction (PCR) from human genomic DNA using highly specific primers, further purified by: 1) cutting the band from a polyacrylamide gel, 2) running a second PCR amplification step, 3) purification using a PCR purification kit (Qiagen Inc., Valencia, Calif.). Before each nanopore experiment, a DNA solution was heated to 70° C. for 10 min and cooled to room temperature.

Nanopores of diameters 2-5 nm were fabricated in 25-30 nm thick, low-stress silicon nitride (SiN) windows (25 μm×25 μm) supported by a Si chip (Protochips Inc., Raleigh, N.C.) using a focused electron beam, Nanopore chips were cleaned and assembled on a custom-designed cell under controlled atmosphere. Following the addition of degassed and filtered 1 M KCl electrolyte (buffered with 10 mM Tris-HCl to pH 8.5), the nanopore cell was placed in a custom-designed controlled-temperature chamber (±0.1° C.), which allows for rapid thermal equilibration (<5 min) and acts as a primary electromagnetic shield. Ag/AgCl electrodes were immersed into each chamber of the cell and connected to an Axon 200B headstage. All measurements were taken inside a dark Faraday cage. DNA was introduced to the cis chamber, and a positive voltage of 300 mV was applied to the trans chamber in all experiments.

DNA translocations were recorded using custom LabVIEW code, permitting either continuous or triggered storage of ion current blockade events. Current signals were digitized at 16-bit resolution with a sampling frequency of 250 kHz, and further low-pass filtered at 70-100 kHz using an analog 4-pole Butterworth filter. To increase translocation throughput, Dynamic Voltage Control (DVC) was used, allowing the applied voltage to be automatically reversed upon prolonged pore blockage, i.e., if the pore is in blocked state over a set time period (1 s). (For details on the experimental apparatus, see: Bates M, Burns M, Meller A (2003) Dynamics of DMA molecules in a membrane channel probed by active control techniques. *Biophysics J* 84:2366-2.372, herein incorporated by reference in its entirety.) While the occurrence of these blocks is rare (<0.1%), the auto-cleat function efficiently "pushes back" the obstructing molecule back to the cis chamber within ~1 s, lowering the likelihood of irreversible pore blocks and permitting data collection over hours or days. Event analysis was carried out using custom LabVIEW code, and statistical analysis was performed using Igor Pro (Wavemetrics, Portland, Oreg.).

Example #2: Articulating Solid-State Nanopores with Proteins

Various solid-state nanopore coating schemes, used in order to embed single α-hemolysin (α-HL) channels inside engineered solid-state nanopores, have been investigated, α-hemolysin is well-known in the art as a β-pore forming dimorphic proteins that exist as soluble monomers and then assembles with other monomers to form multimeric assemblies that constitute the pore. Seven α-Hemolysin monomers come together to create this pore. Selected nanopore coating schemes can be used to affix α-hemolysin monomers on the surface of the aperture comprising the nanopore.

Figure 16:
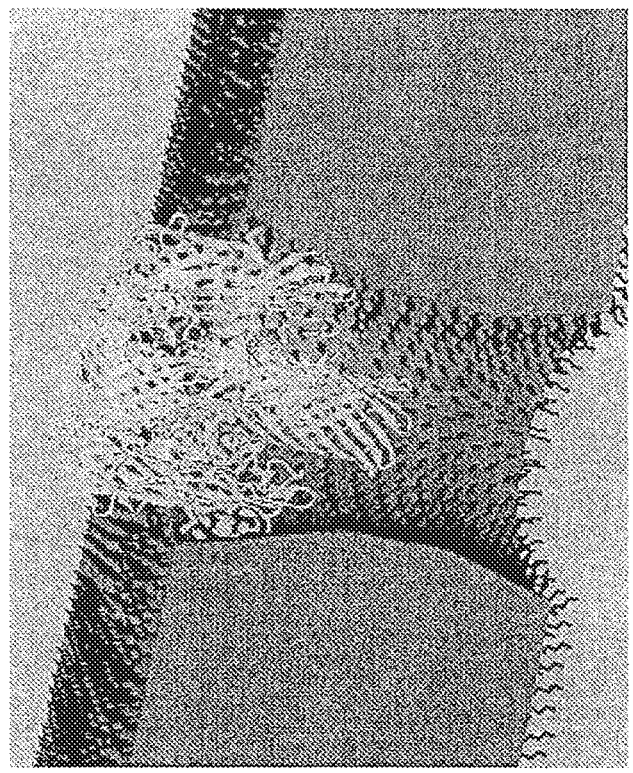
FIG. 16 illustrates schematic representations of a silicon nitride (SiN) solid-state nanopore coated with a self-assembled monolayer, for attachment of a α-Hemolysin channel, according to one embodiment of the invention.

FIG. 16 illustrates schematic representations of a silicon nitride (SiN) solid-state nanopore coated with a self-assembled monolayer, for attachment of a α-Hemolysin channel, according to one embodiment of the invention. FIG. 16 provides a scheme of a silicon nitride (SiN) solid-state nanopore (gray) coated with a self-assembled monolayer (dark), for attachment of a α-Hemolysin channel (light). The organic coating can either be immobilized by chemically reacting with the channel (permanent immobilization) or physical interact ion (temporary immobilization), depending on the terminal group of the organic coating and the channel variant.

At present, experimental success has been achieved with selected types of coatings. Specifically, embedding α-HL inside a 10 nm pore coated with a PEG monolayer (methoxyethylene glycol-terminated silane) has been achieved. After ex situ nanopore coating, the nanopore chip was assembled inside a chamber with 1M KCl on both sides of the nanopore, and α-HL was added to the cis chamber. After 1-2 minutes, the conductance of the pore markedly dropped, indicating pore obstruction. Current-voltage curves were then recorded to verify that the obstruction is an embedded α-HL channel.

Figure 17B:
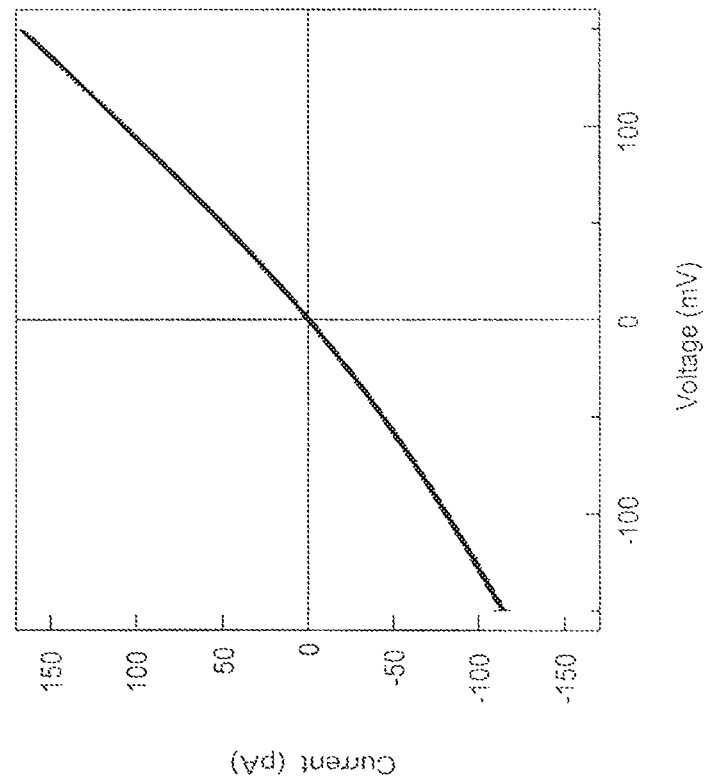
FIG. 17 A-B illustrate plots of current-voltage curves for α-HL embedded in a PEG-coated solid-state nanopore, according to various embodiments of the invention, as compared to a lipid-embedded α-HL channel.
Figure 17A:
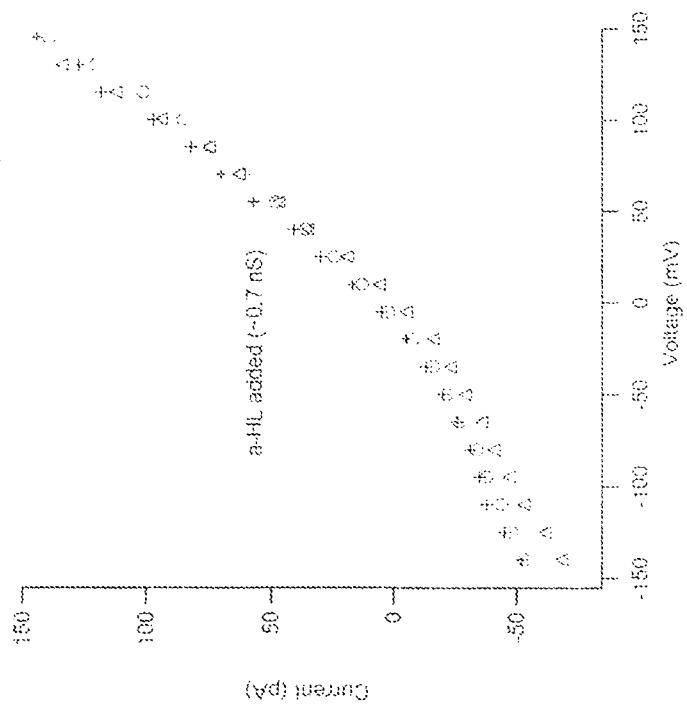

FIGS. 17 A-B illustrate plots of current-voltage curves for α-HL embedded in a PEG-coated solid-state nanopore according to various embodiments of the invention as compared to a lipid-embedded α-HL channel. FIG. 17A shows three current-voltage curves of α-HL embedded in a PEG-coated 10 nm solid-state nanopore (1M KCl, 21° C.). An asymmetric conductance characteristic of a lipid-embedded α-HL channel may be seen with reference to FIG. 17A. FIG. 17B shows a current-voltage curve of a lipid-embedded α-HL channel (1M KCl, 21° C.). These results may be reproduced using different coatings providing preliminary measurements to establish the embedded-nanopore characteristics.

Other Embodiments

In view of the wide variety of embodiments to which the principles of the present invention can be applied, it should foe understood that the illustrated embodiments are exemplary only, and should not be taken as limiting the scope of the present invention. Other embodiments of coated nanopores include: species-selective membranes using chemically modified arrays, immobilization of inorganic particles, and others.

Other aspects, modifications, and embodiments are within the scope of the following claims. The invention may be embodied in other specific forms without departing from the essential characteristics thereof. The present embodiments are therefore considered to be illustrative and not restrictive.

Incorporation by Reference

The entire contents of each of the citations referenced above in the application are herein incorporated by reference.

The invention claimed is:

1. A method for determining nucleotide sequences of polynucleotides, the method comprising the steps of:
providing an optically-addressable nanopore array comprising a solid-state insulating membrane having a plurality of nanopores, wherein the optically-addressable nanopore array separates a cis chamber from a trans chamber and wherein the nanopores are spaced so that fluorescence from adjacent nanopores is spatially resolved;
translocating fluorophore-labeled polynucleotides through the nanopores from the cis chamber to the trans chamber; and
optically probing the nanopore array wherein an optical sensor of a plurality of optical sensors selectively addresses each nanopore in the array to detect fluorescent emission variations as a function of time at each nanopore in the array, and wherein each of said fluorescent emission variations from every nucleotide as a function of time from a nanopore is indicative of a nucleotide sequence of a polynucleotide translocating therethrough.

2. The method of claim 1 wherein each of said nanopores comprises a solid-state nanopore through said membrane and a protein nanopore immobilized therein.

3. The method of claim 2 wherein said protein nanopore is immobilized by an organic chemical coating on said surface.

4. The method of claim 3 wherein said protein nanopore is an α-hemolysin or a mutant thereof.

5. The method of claim 1 wherein said optically-addressable nanopore array has at least a 500 nm spacing between adjacent nanopores.

6. The method of claim 1 wherein said step of optically probing includes collecting said fluorescent emission variations with a microscope.

7. The method of claim 1 wherein said polynucleotide is single stranded DNA.

8. The method of claim 1 wherein said fluorescent emission variations are generated by fluorescence resonance energy transfer (FRET).

9. The method of claim 1 wherein said fluorophore-labeled polynucleotides are charged and are translocated from said cis chamber to said trans chamber by an electric field across said solid-state insulating membrane.

* * * * *